US010858535B2

(12) United States Patent
Retsch, Jr. et al.

(10) Patent No.: US 10,858,535 B2
(45) Date of Patent: *Dec. 8, 2020

(54) COATING COMPOSITION COMPRISING A POWDER DISPERSED IN A LIQUID CARRIER

(71) Applicant: PPG Industries Ohio, Inc., Cleveland, OH (US)

(72) Inventors: William H. Retsch, Jr., Allison Park, PA (US); Anthony M. Chasser, Greensburg, PA (US); Edward R. Millero, Jr., Gibsonia, PA (US); John M. Dudik, Apollo, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 102 days.

This patent is subject to a terminal disclaimer.

(21) Appl. No.: 16/069,580

(22) PCT Filed: Jan. 13, 2017

(86) PCT No.: PCT/IB2017/050189
§ 371 (c)(1),
(2) Date: Jul. 12, 2018

(87) PCT Pub. No.: WO2017/122170
PCT Pub. Date: Jul. 20, 2017

(65) Prior Publication Data
US 2019/0031913 A1    Jan. 31, 2019

Related U.S. Application Data

(63) Continuation of application No. 15/151,547, filed on May 11, 2016, now abandoned, and a continuation of (Continued)

(30) Foreign Application Priority Data

Jan. 15, 2016   (EP) ..................................... 16151619
Jan. 15, 2016   (EP) ..................................... 16151620
Jan. 15, 2016   (EP) ..................................... 16151621

(51) Int. Cl.
| | |
|---|---|
| C09D 175/12 | (2006.01) |
| C09D 5/02 | (2006.01) |
| C09D 5/03 | (2006.01) |
| B27N 7/00 | (2006.01) |
| C08G 18/48 | (2006.01) |
| C08G 18/66 | (2006.01) |
| C08G 18/67 | (2006.01) |
| C08G 18/75 | (2006.01) |
| C08G 18/79 | (2006.01) |
| C08G 18/80 | (2006.01) |

(Continued)

(52) U.S. Cl.
CPC ........... *C09D 175/12* (2013.01); *B27N 7/005* (2013.01); *B65D 1/12* (2013.01); *C07C 275/14* (2013.01); *C07C 275/26* (2013.01); *C08G 18/246* (2013.01); *C08G 18/3275* (2013.01); *C08G 18/348* (2013.01); *C08G 18/48* (2013.01); *C08G 18/4854* (2013.01); *C08G 18/6692* (2013.01); *C08G 18/672* (2013.01); *C08G 18/73* (2013.01); *C08G 18/751* (2013.01); *C08G 18/755* (2013.01); *C08G 18/792* (2013.01); *C08G 18/8041* (2013.01); *C09D 5/02* (2013.01); *C09D 5/03* (2013.01); *C09D 175/02* (2013.01); *C09D 175/16* (2013.01); *B27N 3/002* (2013.01)

(58) Field of Classification Search
CPC .......... C09D 175/12; C09D 5/02; C09D 5/03; C09D 175/16; C09D 175/02; B27N 7/005; B27N 3/002; C08G 18/4854; C08G 18/6692; C08G 18/672; C08G 18/755; C08G 18/792; C08G 18/8041; C08G 18/246; C08G 18/3275; C08G 18/348; C08G 18/73; C08G 18/751; C08G 18/48; B65D 1/12; C07C 275/14; C07C 275/26

See application file for complete search history.

(56) References Cited

U.S. PATENT DOCUMENTS

| | | |
|---|---|---|
| 3,294,751 A | 12/1966 | Beitchman |
| 3,420,787 A | 1/1969 | Reymore et al. |

(Continued)

FOREIGN PATENT DOCUMENTS

| | | |
|---|---|---|
| CN | 1662618 A | 8/2005 |
| CN | 101098935 A | 1/2008 |

(Continued)

OTHER PUBLICATIONS

Machine English translation of CN101098935.
(Continued)

Primary Examiner — Michael C Miggins
(74) Attorney, Agent, or Firm — Diane R. Meyers

(57) ABSTRACT

A metal substrate being coated on at least a portion thereof with a liquid coating composition comprising a powder component dispersed in a liquid carrier, wherein the average particle size of the powder dispersed in the liquid carrier is less than 15 microns (μm); wherein the powder component comprises a thermoset resin; wherein the thermoset resin comprises an acid functional polyester material; and wherein the coating composition is substantially free of bisphenol A (BPA), bisphenol F (BPF), bisphenol A diglycidyl ether (BADGE) and bisphenol F diglycidyl ether (BFDGE).

16 Claims, No Drawings

Related U.S. Application Data application No. 14/996,838, filed on Jan. 15, 2016, now abandoned.

(51) Int. Cl.

| | | |
|---|---|---|
| C08G 18/24 | (2006.01) | |
| C09D 175/16 | (2006.01) | |
| C08G 18/32 | (2006.01) | |
| C08G 18/34 | (2006.01) | |
| C09D 175/02 | (2006.01) | |
| B65D 1/12 | (2006.01) | |
| C07C 275/14 | (2006.01) | |
| C07C 275/26 | (2006.01) | |
| C08G 18/73 | (2006.01) | |
| B27N 3/00 | (2006.01) | |

(56) References Cited

U.S. PATENT DOCUMENTS

| | | |
|---|---|---|
| 3,663,516 A | 5/1972 | Vogt |
| 4,211,683 A | 7/1980 | Wenzel |
| 4,284,572 A | 8/1981 | Stanley et al. |
| 4,990,579 A | 5/1991 | Paar |
| 5,030,754 A | 7/1991 | Speranza et al. |
| 5,047,294 A | 9/1991 | Schwab et al. |
| 5,714,539 A | 2/1998 | Perez et al. |
| 5,858,549 A | 1/1999 | Kielbania, Jr. et al. |
| 5,965,466 A | 10/1999 | Rodrigues et al. |
| 6,051,646 A | 4/2000 | Nass et al. |
| 6,140,388 A | 10/2000 | Nass et al. |
| 6,181,311 B1 | 1/2001 | Hashimoto |
| 6,248,819 B1 | 6/2001 | Masuda et al. |
| 6,290,867 B1 | 9/2001 | Kielbania, Jr. et al. |
| 6,875,800 B2 | 4/2005 | Vanier et al. |
| 6,894,086 B2 | 5/2005 | Munro et al. |
| 7,033,526 B2 | 4/2006 | Figiel et al. |
| 7,605,194 B2 | 10/2009 | Ferencz et al. |
| 8,153,344 B2 | 4/2012 | Faler et al. |
| 8,846,156 B2 | 9/2014 | Swarup et al. |
| 2004/0266921 A1 | 12/2004 | Rodrigues et al. |
| 2005/0171300 A1 | 8/2005 | Moens et al. |
| 2008/0004361 A1 | 1/2008 | Palermo |
| 2009/0197202 A1 | 8/2009 | Matsumura |
| 2009/0246343 A1 | 10/2009 | Wu et al. |
| 2011/0070372 A1 | 3/2011 | Faucher et al. |
| 2011/0070374 A1 | 3/2011 | Ambrose et al. |
| 2011/0151128 A1 | 6/2011 | Boggs et al. |
| 2011/0244157 A1 | 10/2011 | Singer et al. |
| 2014/0011018 A1* | 1/2014 | Diehl ................. C08J 3/05 428/327 |
| 2014/0023782 A1 | 1/2014 | Kunz et al. |
| 2014/0030535 A1 | 1/2014 | Makotky et al. |
| 2014/0319133 A1 | 10/2014 | Castelberg et al. |
| 2015/0344732 A1 | 12/2015 | Witt-Sanson et al. |
| 2016/0280951 A1 | 9/2016 | Drumright et al. |

FOREIGN PATENT DOCUMENTS

| | | |
|---|---|---|
| CN | 102296290 A | 12/2011 |
| CN | 103145588 A | 6/2013 |
| CN | 103502354 A | 1/2014 |
| CN | 104955911 A | 9/2015 |
| EP | 0519186 A1 | 12/1992 |
| EP | 0866082 A1 | 9/1998 |
| EP | 1541640 A1 | 6/2005 |
| EP | 1525274 B1 | 3/2007 |
| EP | 1935878 A1 | 6/2008 |
| EP | 2316868 A1 | 5/2011 |
| EP | 2447059 A2 | 5/2012 |
| EP | 2746353 A1 | 6/2014 |
| EP | 2773710 B1 | 4/2016 |
| JP | 6303007062 B2 | 6/1988 |
| JP | H11335594 A | 12/1999 |
| JP | 2001192609 A | 7/2001 |
| JP | 5146327 B2 | 2/2013 |
| JP | 2014148618 A | 8/2014 |
| RU | 2376284 C1 | 10/2009 |
| RU | 2009103017 A | 8/2010 |
| WO | 2006132910 A1 | 12/2006 |
| WO | 2008076669 A1 | 6/2008 |
| WO | 2009095471 A1 | 8/2009 |
| WO | 2011019840 A1 | 2/2011 |
| WO | 2012118500 A1 | 9/2012 |
| WO | 2012118501 A1 | 9/2012 |
| WO | 2012162301 A1 | 11/2012 |
| WO | 2004000958 A1 | 12/2013 |
| WO | 2013191825 A1 | 12/2013 |
| WO | 2014025411 A1 | 2/2014 |
| WO | 2015077687 A1 | 5/2015 |

OTHER PUBLICATIONS

Machine English translation of CN103145588.
Machine English translation of EP0519186.
Machine English translation of the Abstract only of JP2001192609.
Machine English translation of JPH11335594.
Machine English translation of RU2376284.
Machine English translation of RU2009103017.

* cited by examiner

COATING COMPOSITION COMPRISING A POWDER DISPERSED IN A LIQUID CARRIER

The present invention relates to a coating composition comprising a powder dispersed in a liquid carrier. In particular, the present invention relates to coating composition comprising a powder dispersed in a liquid carrier for coating onto a metal substrate for the packaging industry, such as coating onto food and/or beverage containers.

The surfaces of such food and/or beverage container or aerosol cans are coated for various reasons. The external surfaces of such containers or cans are often coated in a decorative manner and may allow printing thereon to inform a user as to the contents of the container or can. The internal surfaces of such container or cans are typically coated to protect the container or can from the contents therein, which in some instances may be chemically aggressive. The coating on the container or can should also protect the contents from the container or can. There should be a minimal amount of alteration to the contents from materials that are products of erosion of the container or can, or from the coating itself. Accordingly, the coating composition used to coat the internal surfaces of the container or can should be designed such that it is able to withstand contact with these aggressive chemicals and to minimise the release of material from the metal of the container or can or the coating layer into the contents of the container or can.

A wide variety of coatings have been used to coat the above mentioned containers or cans. With regard to food and/or beverage containers, the coating compositions are required to have certain properties such as being capable of high speed application, having excellent adhesion to the substrate, being safe for food contact and having properties once cured that are suitable for their end use.

Many of the coating compositions currently used for food and/or beverage applications contain epoxy resins. Such epoxy resins are typically formed from polyglycidyl ethers of bisphenol A (BPA). BPA is perceived as being harmful to human health and it is therefore desirable to eliminate it from coatings. Derivatives of BPA such as diglycidyl ethers of bisphenol A (BADGE), epoxy novolak resins and polyols prepared from BPA and bisphenol F (BPF) are also viewed as problematic.

According to a first aspect of the present invention there is provided a metal substrate being coated on at least a portion thereof with a liquid coating composition comprising a powder component dispersed in a liquid carrier, wherein the average particle size of the powder dispersed in the liquid carrier is less than 15 microns (μm); wherein the powder component comprises a thermoset resin; wherein the thermoset resin comprises an acid functional polyester material; and wherein the coating composition is substantially free of bisphenol A (BPA), bisphenol F (BPF), bisphenol A diglycidyl ether (BADGE) and bisphenol F diglycidyl ether (BFDGE).

"Powder", and like terms as used herein, refers to materials that are in the form of solid particulates, as opposed to materials which are in the liquid form.

The coating compositions of the present invention comprise a powder component. The powder component comprises a thermoset resin. The thermoset resin comprises an acid functional polyester material. Suitably, the acid functional polyester material may comprise the reaction product of a polyacid and a polyol.

"Polyacid", and like terms as used herein, refers to a compound having two or more carboxylic acid groups, such as two, three or four acid groups, and includes an ester of the polyacid (wherein one or more of the acid groups is esterified) or an anhydride. The polyacid is suitably an organic polyacid.

"Diacid", and like terms as used herein, refers to a compound having two carboxylic acid groups and includes an ester of the diacid (wherein one or more of the acid groups is esterified) or an anhydride. The diacid is suitably an organic diacid.

Suitably, the carboxylic acid groups of the polyacid may be connected by a bridging group selected from: an alkylene group; an alkenylene group; an alkynylene group; or an arylene group.

The acid functional polyester material may be formed from any suitable polyacid. Suitable examples include, but are not limited to one or more of the following: diacids such as, for example, maleic acid, fumaric acid, itaconic acid, adipic acid, azelaic acid, succinic acid, sebacic acid, glutaric acid, heptanoic acid, decanoic diacid, dodecanoic diacid, dodecanedioic acid, phthalic acid, isophthalic acid, 5-tert-butylisophthalic acid, tetrachlorophthalic acid, tetrahydrophthalic acid, naphthalene dicarboxylic acid, terephthalic acid, hexahydrophthalic acid, methylhexahydrophthalic acid, dimethyl terephthalate, cyclohexane dicarboxylic acid, chlorendic anhydride, 1,3-cyclohexane dicarboxylic acid, 1,4-cyclohexane dicarboxylic acid, endomethylene tetrahydrophthalic acid and endoethylene hexahydrophthalic acid; triacids such as, for example, trimellitic acid; polyacids such as, for example, naphthalene tetracarboxylic acid, cyclohexanetetra carboxylic acid, cyclobutane tetracarboxylic and tricyclodecane polycarboxylic acid; esters and anhydrides of all the aforementioned acids and combinations thereof.

The polyacid may be selected from terephthalic acid; isophthalic acid; adipic acid; trimellitic anhydride; or combinations thereof.

The polyacid may comprise terephthalic acid and/or isophthalic acid. The polyacid may comprise at least 50 mol %, suitably at least 60 mol %, such as at least 70 mol %, or even at least 75 mol % of terephthalic acid and/or isophthalic acid based on the total number of moles of polyacid. The polyacid may comprise up to 100 mol %, suitably up to 95 mol %, such as up to 90 mol % of terephthalic acid and/or isophthalic acid based on the total number of moles of polyacid. The polyacid may comprise from 50 to 100 mol %, suitably from 60 to 100 mol %, such as from 70 to 100 mol %, or even from 75 to 100 mol % of terephthalic acid and/or isophthalic acid based on the total number of moles of polyacid. The polyacid may comprise from 50 to 95 mol %, suitably from 60 to 95 mol %, such as from 70 to 95 mol %, or even from 75 to 95 mol % of terephthalic acid and/or isophthalic acid based on the total number of moles of polyacid. The polyacid may comprise from 50 to 90 mol %, suitably from 60 to 90 mol %, such as from 70 to 90 mol %, or even from 75 to 90 mol % of terephthalic acid and/or isophthalic acid based on the total number of moles of polyacid. Suitably, the polyacid may comprise from 75 to 90 mol % of terephthalic acid and/or isophthalic acid based on the total number of moles of polyacid.

The polyacid may comprise a diacid. The diacid may comprise at least 60 mol %, suitably at least 70 mol %, such as at least 80 mol %, or even 85 mol % of terephthalic acid and/or isophthalic acid based on the total number of moles of diacid. The diacid may comprise up to 100 mol %, suitably up to 99.9 mol %, such as at least 99 mol %, or even up to 95 mol % of terephthalic acid and/or isophthalic acid based on the total number of moles of diacid. The polyacid may comprise from 60 to 100 mol %, suitably from 70 to 100 mol %, such as from 80 to 100 mol %, or even from 80 to 100 mol % of terephthalic acid and/or isophthalic acid based on the total number of moles of diacid. The polyacid may comprise from 60 to 99.9 mol %, suitably from 70 to 99.9 mol %, such as from 80 to 99.9 mol %, or even from 80 to 99.9 mol % of terephthalic acid and/or isophthalic acid based on the total number of moles of diacid. The polyacid may comprise from 60 to 99 mol %, suitably from 70 to 99 mol %, such as from 80 to 99 mol %, or even from 80 to 99 mol % of terephthalic acid and/or isophthalic acid based on the total number of moles of diacid. The polyacid may comprise from 60 to 95 mol %, suitably from 70 to 95 mol %, such as from 80 to 95 mol %, or even from 80 to 95 mol % of terephthalic acid and/or isophthalic acid based on the total number of moles of diacid. Suitably, the diacid may comprise from 75 to 100 mol % of terephthalic acid and/or isophthalic acid based on the total number of moles of diacid.

The acid functional polyester material may be formed from a polyacid comprising succinic acid, glutaric acid, adipic acid, heptanoic acid, dodecanedioic acid or combinations thereof.

Suitably, the acid functional polyester material may be formed from a polyacid comprising succinic acid adipic acid, dodecanedioic acid or combinations thereof. It has surprisingly and advantageously been found by the present inventors that the presence of such polyacids in an acid functional polyester material results in a liquid coating composition, comprising such acid functional polyester materials, having a lower curing temperature than would typically be expected. It will be understood by a person skilled in the art that this is advantageous industrially and environmentally.

"Polyol" and like terms, as used herein, refers to a compound having two or more hydroxyl groups, such as two, three or four hydroxyl groups. The hydroxyl groups of the polyol may be connected by a bridging group selected from: an alkylene group; an alkenylene group; an alkynylene group; or an arylene group. Suitably the polyol is an organic polyol.

"Diol" and like terms, as used herein, refers to a compound having two hydroxyl groups. The hydroxyl groups of the diol may be connected by a bridging group selected from: an alkylene group; an alkenylene group; an alkynylene group; or an arylene group. Suitably the diol is an organic polyol.

The acid functional polyester material may be formed from any suitable polyol. Suitable examples include, but are not limited to one or more of the following: diols such as, for example, alkylene glycols, such as ethylene glycol, diethylene glycol, dipropylene glycol, triethylene glycol, tripropylene glycol, hexylene glycol, polyethylene glycol, polypropylene glycol and neopentyl glycol; hydrogenated bisphenol A; cyclohexanediol; propanediols including 1,2-propanediol, 1,3-propanediol, butyl ethyl propanediol and 2-ethyl-2-butyl-1,3-propanediol; butanediols including 1,4-butanediol, 1,3-butanediol, butane-2,3-diol, 2-methyl-1,3-propanediol, tricyclodecane dimethanol-2,2,4,4-tetramethyl cyclobutane-1,3-diol and 2-ethyl-1,4-butanediol; pentanediols including trimethyl pentanediol and 2-methylpentanediol; cyclohexanedimethanol; hexanediols including 1,6-hexanediol, caprolactonediol (for example, the reaction product of epsilon-capro lactone and ethylene glycol); hydroxyalkylated bisphenols; polyether glycols, for example, poly(oxytetramethylene) glycol; dimethylol cyclohexane; triols such as, for example, trimethylol propane, trimethylol ethane, trimethylol butane and glycerol; polyols such as, for example, pentaerythritol and di-pentaerythritol; and the like or combinations thereof.

The acid functional polyester material may be formed from an unsaturated polyol. Suitable examples of unsaturated polyols include, but are not limited to one or more of the following: trimethylol propane monoallyl ether; trimethylol ethane monoallyl ether; prop-1-ene-1,3-diol or combinations thereof.

The polyol may be selected from neopentyl glycol; ethylene glycol; diethylene glycol; or combinations thereof.

The polyol may comprise neopentyl gylcol. The polyol may comprise at least 10 mol %, suitably at least 20 mol %, such as at least 30 mol %, such as 40 mol %, or even at least 50 mol % of neopentyl glycol based on the total number of moles of polyol. The polyol may comprise up to 100 mol %, suitably up to 90 mol %, such as up to 80 mol %, or even up to 70 mol % of neopentyl glycol based on the total number of moles of polyol present. The polyol may comprise from 10 to 100 mol %, suitably from 10 to 90 mol %, such as from 10 to 80 mol %, or even from 10 to 70 mol % of neopentyl glycol based on the total number of moles of polyol present. The polyol may comprise from 20 to 100 mol %, suitably from 20 to 90 mol %, such as from 20 to 80 mol %, or even from 20 to 70 mol % of neopentyl glycol based on the total number of moles of polyol present. The polyol may comprise from 30 to 100 mol %, suitably from 30 to 90 mol %, such as from 30 to 80 mol %, or even from 30 to 70 mol % of neopentyl glycol based on the total number of moles of polyol present. The polyol may comprise from 40 to 100 mol %, suitably from 40 to 90 mol %, such as from 40 to 80 mol %, or even from 40 to 70 mol % of neopentyl glycol based on the total number of moles of polyol present. The polyol may comprise from 50 to 100 mol %, suitably from 50 to 90 mol %, such as from 50 to 80 mol %, or even from 50 to 70 mol % of neopentyl glycol based on the total number of moles of polyol present. Suitably, the polyol may comprise from 50 to 70 mol % of neopentyl glycol based on the total number of moles of polyol present.

The polyol may comprise a diol. The diol may comprise at least 10 mol %, suitably at least 20 mol %, such as at least 30 mol %, such as 40 mol %, or even at least 50 mol % of neopentyl glycol based on the total number of moles of diol. The diol may comprise up to 100 mol %, suitably up to 90 mol %, such as up to 80 mol %, or even up to 70 mol % of neopentyl glycol based on the total number of moles of diol present. The diol may comprise from 10 to 100 mol %, suitably from 10 to 90 mol %, such as from 10 to 80 mol %, or even from 10 to 70 mol % of neopentyl glycol based on the total number of moles of diol present. The diol may comprise from 20 to 100 mol %, suitably from 20 to 90 mol %, such as from 20 to 80 mol %, or even from 20 to 70 mol % of neopentyl glycol based on the total number of moles of diol present. The diol may comprise from 30 to 100 mol %, suitably from 30 to 90 mol %, such as from 30 to 80 mol %, or even from 30 to 70 mol % of neopentyl glycol based on the total number of moles of diol present. The diol may comprise from 40 to 100 mol %, suitably from 40 to 90 mol %, such as from 40 to 80 mol %, or even from 40 to 70 mol % of neopentyl glycol based on the total number of moles of diol present. The diol may comprise from 50 to 100 mol %, suitably from 50 to 90 mol %, such as from 50 to 80 mol %, or even from 50 to 70 mol % of neopentyl glycol based on the total number of moles of diol present. Suitably, the diol may comprise from 50 to 70 mol % of neopentyl glycol based on the total number of moles of diol present.

The term "alk" or "alkyl", as used herein unless otherwise defined, relates to saturated hydrocarbon radicals being straight, branched, cyclic or polycyclic moieties or combinations thereof and contain 1 to 20 carbon atoms, suitably 1 to 10 carbon atoms, more suitably 1 to 8 carbon atoms, still more suitably 1 to 6 carbon atoms, yet more suitably 1 to 4 carbon atoms. These radicals may be optionally substituted with a chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from methyl, ethyl, n-propyl, isopropyl, n-butyl, isobutyl, sec-butyl, tert-butyl, 2-methylbutyl, pentyl, iso-amyl, hexyl, cyclohexyl, 3-methylpentyl, octyl and the like. The term "alkylene", as used herein, relates to a bivalent radical alkyl group as defined above. For example, an alkyl group such as methyl which would be represented as —$CH_3$, becomes methylene, —$CH_2$—, when represented as an alkylene. Other alkylene groups should be understood accordingly.

The term "alkenyl", as used herein, relates to hydrocarbon radicals having one or several, suitably up to 4, double bonds, being straight, branched, cyclic or polycyclic moieties or combinations thereof and containing from 2 to 18 carbon atoms, suitably 2 to 10 carbon atoms, more suitably from 2 to 8 carbon atoms, still more suitably 2 to 6 carbon atoms, yet more suitably 2 to 4 carbon atoms. These radicals may be optionally substituted with a hydroxyl, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. The term "alkenylene", as used herein, relates to a bivalent radical alkenyl group as defined above. For example, an alkenyl group such as ethenyl which would be represented as —CH=CH2, becomes ethenylene, —CH=CH—, when represented as an alkenylene. Other alkenylene groups should be understood accordingly.

The term "alkynyl", as used herein, relates to hydrocarbon radicals having one or several, suitably up to 4, triple bonds, being straight, branched, cyclic or polycyclic moieties or combinations thereof and having from 2 to 18 carbon atoms, suitably 2 to 10 carbon atoms, more suitably from 2 to 8 carbon atoms, still more suitably from 2 to 6 carbon atoms, yet more suitably 2 to 4 carbon atoms. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsiloxane groups. Examples of such radicals may be independently selected from alkynyl radicals include ethynyl, propynyl, propargyl, butynyl, pentynyl, hexynyl and the like. The term "alkynylene", as used herein, relates to a bivalent radical alkynyl group as defined above. For example, an alkynyl group such as ethynyl which would be represented as —C≡CH, becomes ethynylene, —C≡C—, when represented as an alkynylene. Other alkynylene groups should be understood accordingly.

The term "aryl" as used herein, relates to an organic radical derived from an aromatic hydrocarbon by removal of one hydrogen, and includes any monocyclic, bicyclic or polycyclic carbon ring of up to 7 members in each ring, wherein at least one ring is aromatic. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsilcon groups. Examples of such radicals may be independently selected from phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, tetrahydronaphthyl, indanyl, biphenyl, phenanthryl, anthryl or acenaphthyl and the like. The term "arylene", as used herein, relates to a bivalent radical aryl group as defined above. For example, an aryl group such as phenyl which would be represented as -Ph, becomes phenylene, -Ph-, when represented as an arylene. Other arylene groups should be understood accordingly.

For the avoidance of doubt, the reference to alkyl, alkenyl, alkynyl, aryl or aralkyl in composite groups herein should be interpreted accordingly, for example the reference to alkyl in aminoalkyl or alk in alkoxyl should be interpreted as alk or alkyl above etc.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. Singular encompasses plural and vice versa. For example, although reference is made herein to, for example, "a" liquid coating, "a" thermoset powder component, "a" liquid carrier, "an" alkanol amine, "the" residue of "an", and the like, one or more of each of these and any other components can be used. As used herein, the term "polymer" refers to oligomers and both homopolymers and copolymers, and the prefix "poly" refers to two or more. Including, for example and like terms means including for example but not limited to. When ranges are given, any endpoints of those ranges and/or numbers within those ranges can be.

The acid functional polyester material may be formed from any suitable molar ratio of polyacid to polyol. The molar ratio of polyacid to polyol in the polyester material may be from 20:1 to 1:20, suitably from 10:1 to 1:10, such as from 5:1 to 1:5, or even from 2:1 to 1:2. Suitably, the molar ratio of polyacid to polyol in the acid functional polyester material may be 1:1.

The acid functional polyester material may comprise a diacid, a triacid and a diol. It will be appreciated by a person skilled in the art that the amount of triacid present will influence the acid number of the acid functional polyester material.

The acid functional polyester material may optionally be formed from one or more additional monomers. Suitably, the acid functional polyester material may optionally include one or more additional monomers selected from monoacids or monohydric alcohols or combinations thereof. Suitably, the optional additional monomers may be organic.

The acid functional polyester material may optionally be formed from an additional monoacid. "Monoacid", and like terms as used herein, refers to compounds having one carboxylic acid group and includes an ester of the monoacid (where the acid group is esterified) or an anhydride. The monoacid is suitably an organic monoacid.

The acid functional polyester material may optionally be formed from any suitable additional monoacid. Suitable examples include, but are not limited to one or more of the following: benzoic acid; cyclohexane carboxylic acid; tricyclodecane carboxylic acid; camporic acid; benzoic acid; t-butyl benzoic acid; $C_1$-$C_{18}$ aliphatic carboxylic acids such as acetic acid; propanoic acid; butanoic acid; hexanoic acid; oleic acid; linoleic acid; undecanoic acid; lauric acid; isononanoic acid; fatty acids; hydrogenated fatty acids of naturally occurring oils; esters and/or anhydrides of any of the aforementioned acids and combinations thereof.

The acid functional polyester material may optionally be formed from an additional monohydric alcohol. "Monohydric alcohol" and like terms as used herein, refers to compounds having one hydroxyl group. Suitably, the monohydric alcohol is an organic monohydric alcohol.

The acid functional polyester material may optionally be formed from any suitable additional monohydric alcohol. Suitable examples include but are not limited to one or more of the following: benzyl alcohol; hydroxyethoxybenzene; methanol; ethanol; propanol; butanol; pentanol; hexanol; heptanol; dodecyl alcohol; stearyl alcohol; oleyl alcohol; undecanol; cyclohexanol; phenol; phenyl carbinol; methylphenyl carbinol; cresol; monoethers of glycols; halogen-substituted or other substituted alcohols and combinations thereof.

The acid functional polyester material may have an acid number (AN) of at least 25 mg KOH/g. Suitably, the polyester material may have an acid number from 25 to 100 mg KOH/g, such as from 30 to 100 mg KOH/g or even from 50 to 90 mg KOH/g. The acid functional polyester material may have an acid number from 50 to 80 mg KOH/g.

The acid functional polyester material may have an acid number from 65 to 75 mg KOH/g.

The acid functional polyester material may have an acid number from 30 to 40 mg KOH/g.

Suitably, the acid number (AN) is expressed on solids.

The acid number (AN) of the acid functional polyester material may be measured by any suitable method. Methods to measure AN will be well known to a person skilled in the art. Suitably, the AN is determined by titration with 0.1M methanolic potassium hydroxide (KOH) solution. A sample of solid polyester (typically, 0.1 to 3 g) is weighed accurately into a conical flask and is dissolved, using light heating and stirring as appropriate, in 25 ml of dimethyl formamide containing phenolphthalein indicator. The solution is then cooled to room temperature and titrated with the 0.1M methanolic potassium hydroxide solution. The resulting acid number is expressed in units of mg KOH/g and is calculated using the following equation:

$$\text{Acid number} = \frac{\text{titre of KOH solution (ml)} \times \text{molarity KOH solution (M)} \times 56.1}{\text{weight of solid sample (g)}}$$

The acid functional polyester material may have any suitable gross hydroxyl value (OHV). The acid functional polyester material may have a gross OHV up to 5.0 mg KOH/g. Suitably, the acid functional polyester material may have a gross OHV from 0 to 5.0 mg KOH/g, such as from 0 to 0.4 KOH/g or even from 0 to 3.0 KOH/g.

All values for acid number (AN) reported herein were measured this way.

Suitably, the hydroxyl value (OHV) is expressed on solids.

The hydroxyl value (OHV) of the acid functional polyester material may be measured by any suitable method. Methods to measure OHV will be well known to a person skilled in the art. Suitably, the hydroxyl value is the number of mg of KOH equivalent to the hydroxyl groups in 1 g of material. Suitably, a sample of solid polyester (typically, 0.1 to 3 g) is weighed accurately into a conical flask and is dissolved, using light heating and stirring as appropriate, in 20 ml of tetrahydrofuran. 10 ml of 0.1M 4-(dimethylamino) pyridine in tetrahydrofuran (catalyst solution) and 5 ml of a 9 vol % solution of acetic anhydride in tetrahydrofuran (i.e. 90 ml acetic anhydride in 910 ml tetrahydrofuran; acetylating solution) are then added to the mixture. After 5 minutes, 10 ml of an 80 vol % solution of tetrahydrofuran (i.e. 4 volume parts tetrahydrofuran to 1 part distilled water; hydrolysis solution) us added. After 15 minutes, 10 ml tetrahydrofuran is added and the solution is titrated with 0.5M ethanolic potassium hydroxide (KOH). A blank sample is also run where the sample of solid polyester is omitted. The resulting hydroxyl number is expressed in units of mg KOH/g and is calculated using the following equation:

$$\text{Hydroxyl value} = \frac{(V_2 - V_1) \times \text{molarity of KOH solution (M)} \times 56.1}{\text{weight of solid sample (g)}}$$

wherein $V_1$ is the titre of KOH solution (ml) of the polyester sample and $V_2$ is the titre of KOH solution (ml) of the blank sample.

All values for gross hydroxyl value (OHV) reported herein were measured this way.

The acid functional polyester material may have any suitable glass transition temperature (Tg). The acid functional polyester material may have a Tg of at least 20° C., suitably at least 30° C., such as at least 40° C., or even at least 50° C. The acid functional polyester material may have a Tg of up to 150° C., suitably up to 120° C., such as up to 100° C., or even up to 80° C. The acid functional polyester material may have a Tg from 20° C. to 150° C., suitably from 20° C. to 120° C., such as from 20° C. to 100° C., or even from 20° C. to 80° C. The acid functional polyester material may have a Tg from 30° C. to 150° C., suitably from 30° C. to 120° C., such as from 30° C. to 100° C., or even from 30° C. to 80° C. The acid functional polyester material may have a Tg from 40° C. to 150° C., suitably from 40° C. to 120° C., such as from 40° C. to 100° C., or even from 40° C. to 80° C. The acid functional polyester material may have a Tg from 50° C. to 150° C., suitably from 50° C. to 120° C., such as from 50° C. to 100° C., or even from 50° C. to 80° C.

The acid functional polyester material may have a Tg from 60° C. to 70° C.

The Tg of the acid functional polyester material may be measured by any suitable method.

Methods to measure Tg will be well known to a person skilled in the art. Suitably, the Tg is measured according to ASTM D6604-00(2013) ("Standard Practice for Glass Transition Temperatures of Hydrocarbon Resins by Differential Scanning calorimetry". Heat-flux differential scanning calorimetry (DSC), sample pans: aluminium, reference: blank, calibration: indium and mercury, sample weight: 10 mg, heating rate: 20° C./min). All values for glass transition temperature (Tg) reported herein were measured this way.

The acid functional polyester material of the present invention may have any suitable viscosity at 200° C. The acid functional polyester material may have a viscosity at 200° C. from 2 to 100 Poise, suitably from 5 to 70 Poise, such as from 10 to 50 Poise, or even from 20 to 40 Poise. The acid functional polyester material may have a viscosity at 200° C. of at least 2 Poise, suitably at least 5 Poise, such as at least 10 Poise, or even at least 20 Poise. The acid functional polyester material may have a viscosity at 200° C. of up to 100 Poise, suitably up to 70 Poise, such as up to 50 Poise, or even up to 40 Poise. The acid functional polyester material may have a viscosity at 200° C. from 2 to 100 Poise, suitably from 2 to 70 Poise, such as from 2 to 50 Poise, or even from 2 to 40 Poise. The acid functional polyester material may have a viscosity at 200° C. from 5 to 100 Poise, suitably from 5 to 70 Poise, such as from 5 to 50 Poise, or even from 5 to 40 Poise. The acid functional polyester material may have a viscosity at 200° C. from 10 to 100 Poise, suitably from 10 to 70 Poise, such as from 10 to 50 Poise, or even from 10 to 40 Poise. The acid functional polyester material may have a viscosity at 200° C. from 20 to 100 Poise, suitably from 20 to 70 Poise, such as from 20 to 50 Poise, or even from 20 to 40 Poise.

The melt viscosity of the acid functional polyester material may be measured by any suitable method. Methods to measure melt viscosity will be well known to a person skilled in the art. Suitably, melt viscosity is determined using a cone and plate viscometer with a heated plate with cones which can be selected together with appropriate rotational speeds to measure viscosities within the desired ranges. Suitably, a Brookfield CAP 2000+ machine which is capable of measuring viscosities at temperatures of 100 to 250° C. is used. The temperature selected for the measurement is held constant throughout the measurement time and the detail of the temperature used is suitably recorded for each measurement. Suitably, the cone used is a spindle no. 6 and the speed of rotation should be selected so as to ensure that the range of measurements falls well within the total measurement range. All values for melt viscosity reported herein were measured this way.

The acid functional polyester material of the present invention may have any suitable number-average molecular weight (Mn). The acid functional polyester material may have an Mn from 500 Daltons (Da=g/mole), suitably from 1,000 Da, such as from 2,000 Da or even from 5,000 Da. The acid functional polyester material may have an Mn up to 200,000 Da, suitably up to 100,000 Da, such as up to 50,000 Da or even up to 20,000 Da.

The acid functional polyester material may have an Mn from 500 to 200,000 Da, suitably from 1,000 to 200,000 Da, such as from 2,000 to 200,000 Da or even from 5,000 to 200,000 Da.

The acid functional polyester material may have an Mn from 500 to 100,000 Da, suitably from 1,000 to 100,000 Da, such as from 2,000 to 100,000 Da or even from 5,000 to 100,000 Da. The acid functional polyester material may have an Mn from 500 to 50,000 Da, suitably from 1,000 to 50,000 Da, such as from 2,000 to 50,000 Da or even from 5,000 to 50,000 Da. The acid functional polyester material may have an Mn from 500 to 20,000 Da, suitably from 1,000 to 20,000 Da, such as from 2,000 to 20,000 Da or even from 5,000 to 20,000 Da.

The number-average molecular weight may be measured by any suitable method. Techniques to measure the number-average molecular weight will be well known to a person skilled in the art. Suitably, the Mn may be determined by gel permeation chromatography using a polystyrene standard according to ASTM D6579-11("Standard Practice for Molecular Weight Averages and Molecular Weight Distribution of Hydrocarbon, Rosin and Terpene Resins by Size Exclusion Chromatography". UV detector; 254 nm, solvent: unstabilised THF, retention time marker: toluene, sample concentration: 2 mg/ml). All values for number-average molecular weight (Mn) reported herein were measured this way.

The acid functional polyester material of the present invention may have any suitable weight-average molecular weight (Mw). The acid functional polyester material may have an Mw from 500 Daltons (Da=g/mole), suitably from 1,000 Da, such as from 2,000 Da or even from 5,000 Da. The acid functional polyester material may have an Mw up to 200,000 Da, suitably up to 100,000 Da, such as up to 50,000 Da or even up to 20,000 Da.

The acid functional polyester material may have an Mw from 500 to 200,000 Da, suitably from 1,000 to 200,000 Da, such as from 2,000 to 200,000 Da or even from 5,000 to 200,000 Da. The acid functional polyester material may have an Mw from 500 to 100,000 Da, suitably from 1,000 to 100,000 Da, such as from 2,000 to 100,000 Da or even from 5,000 to 100,000 Da. The acid functional polyester material may have an Mw from 500 to 50,000 Da, suitably from 1,000 to 50,000 Da, such as from 2,000 to 50,000 Da or even from 5,000 to 50,000 Da. The acid functional polyester material may have an Mw from 500 to 20,000 Da, suitably from 1,000 to 20,000 Da, such as from 2,000 to 20,000 Da or even from 5,000 to 20,000 Da.

A person skilled in the art will appreciate that techniques to measure the number-average molecular weight may also be applied to measure the weight-average molecular weight. All values for weight-average molecular weight (Mw) reported herein were measured this way.

The acid functional polyester material may be in solid form at room temperature and at atmospheric pressure.

The powder component may comprise an optional thermoplastic resin. The thermoplastic resin, when present, may comprise any suitable thermoplastic resin. Suitable examples of thermoplastic resins include, but are not limited to, one ore more of the following: epoxy resins; polyester resins; polyolefin resins; polyurethane resins; polysiloxane resins; acrylic resins; hydrocarbon resins; polyamide resins or combinations thereof. Suitably, the thermoplastic resin may comprise polyolefin resins, acrylic resins or a combination thereof.

The thermoplastic resin, when present, may comprise a polyolefin resin. The thermoplastic resin, when present, may comprise an acrylic resin.

The thermoplastic resin, when present, may comprise a polyolefin resin and an acrylic resin.

The thermoplastic resin, when present, may have any suitable glass transition temperature (Tg). The thermoplastic resin may have a Tg of at least 20° C., suitably at least 25° C., such as at least 30° C., or even at least 40° C. The thermoplastic resin may have a Tg of up to 150° C., suitably up to 120° C., such as up to 100° C., or even up to 80° C. The thermoplastic resin may have a Tg from 20° C. to 150° C., suitably from 20° C. to 120° C., such as from 20° C. to 100° C., or even from 20° C. to 80° C. The thermoplastic resin may have a Tg from 25° C. to 150° C., suitably from 25° C. to 120° C., such as from 25° C. to 100° C., or even from 25° C. to 80° C. The thermoplastic resin may have a Tg from 30° C. to 150° C., suitably from 30° C. to 120° C., such as from 30° C. to 100° C., or even from 30° C. to 80° C. The thermoplastic resin may have a Tg from 40° C. to 150° C., suitably from 40° C. to 120° C., such as from 40° C. to 100° C., or even from 40° C. to 80° C.

Suitably, the thermoplastic resin, when present, may have a Tg from 40 to 80° C.

The thermoplastic resin, when present, may have a Tg from 40 to 70° C.

The Tg of the thermoplastic resin, when present, may be measured by any suitable method. Methods to measure Tg will be well known to a person skilled in the art. Suitably, the Tg is measured according to ASTM D6604-00(2013) ("Standard Practice for Glass Transition Temperatures of Hydrocarbon Resins by Differential Scanning calorimetry". Heat-flux differential scanning calorimetry (DSC), sample pans: aluminium, reference: blank, calibration: indium and mercury, sample weight: 10 mg, heating rate: 20° C./min). All glass transition temperatures (Tg) reported herein were measured this way.

The thermoplastic resin of the present invention suitably has a melt index (MI) between 2 and 50 g per 10 min. Where the thermoplastic resin comprises polyamide, the polyamide suitable has a melt index of between 27 and 50 g per 10 min.

The melt index is measured according to ISO 1133-1: 2011 method B (displacement-measurement method) at a temperature of 230° C. and a nominal load of 2.66 kg. All values for melt index reported herein were measured this way.

The thermoplastic resin, when present, may comprise a commercially available thermoplastic resin such as nylon resins, for example, or those available under the trade name Surlyn (available from DuPont).

The thermoplastic resin may be provided in the form of a granular solid or in the form of a dispersion in a liquid carrier.

When the thermoplastic resin is provided in the form of a granular solid, the granular solid may be formed by any suitable method. The granular solid thermoplastic resin, may be extruded in combination with the thermoset material. Suitable methods will be well known to a person skilled in the art. Suitably, the extruded thermoset and thermoplastic resin is ground to a powder.

The thermoplastic resin, when present, may comprise a polyolefin resin granular solid.

The thermoplastic resin, when present, may comprise an acrylic resin granular solid.

The thermoplastic resin, when present, may comprise a polyolefin resin powder and an acrylic resin granular solid.

For the avoidance of doubt, a dispersion is a granular solid, such as a powder suspended in a liquid carrier. The liquid carrier, when present, may comprise water, an organic solvent, a mixture of water and one or more organic solvent(s) or a mixture of organic solvents. Suitably, the liquid carrier may comprise water.

Suitable organic solvents include, but are not limited to one or more of the following: aliphatic hydrocarbons such as mineral spirits and high flash point naphtha; aromatic hydrocarbons such as benzene; toluene; xylene; solvent naphtha 100, 150, 200; those available from Exxon-Mobil Chemical Company under the SOLVESSO trade name; alcohols such as ethanol; n-propanol; isopropanol; and n-butanol; ketones such as acetone; cyclohexanone; methylisobutyl ketone; methyl ethyl ketone; esters such as ethyl acetate; butyl acetate; n-hexyl acetate; glycols such as butyl glycol; glycol ethers such as methoxypropanol; ethylene glycol monomethyl ether; ethylene glycol monobutyl ether and combinations thereof.

The thermoplastic resin, when present, may comprise a polyolefin resin, an acrylic resin or a combination thereof dispersed in a liquid carrier. Suitably, the thermoplastic resin, when present, may comprise a polyolefin resin, an acrylic resin or a combination thereof dispersed in water.

The thermoplastic resin, when present, may comprise a polyolefin resin dispersed in a liquid carrier, suitably dispersed in water.

The thermoplastic resin, when present, may comprise an acrylic resin dispersed in a liquid carrier, suitably dispersed in water.

The thermoplastic resin, when present, may comprise a polyolefin resin and an acrylic resin dispersed in a liquid carrier, suitably dispersed in water.

It will be appreciated by a person skilled in the art that when the thermoplastic resin, when present, is provided in the form of a dispersion, the liquid carrier of the thermoplastic resin dispersion may form some or all of the liquid carrier of the present invention.

The powder component of the present invention may further comprise an optional crosslinker material. The crosslinker material, when present, may comprise any suitable crosslinker material. Suitable crosslinker materials, when present, will be well known to the person skilled in the art. Suitable crosslinker materials include, but are not limited to one or more of the following: phenolic resins (or phenol-formaldehyde resins); aminoplast resins (or triazine-formaldehyde resins); amino resins; epoxy resins; epoxy-mimic resins, such as those based on bisphenols and other bisphenol A (BPA) replacements; isocyanate resins, isocyanurate resins, such as triglycidylisocyanurate; hydroxy (alkyl) amide resins, such as β-hydroxy (alkyl) amide resins; hydroxy(alkyl) urea resins; carbodiimide resins; oxazolines; polyamines; polyamides and combinations thereof.

The crosslinker material, when present, may be selected from hydroxy (alkyl) amide resins, such as β-hydroxy (alkyl) amide resins; hydroxy(alkyl) urea resins; carbodiimide resins; oxazolines; isocyanurate resins, such as triglycidylisocyanurate; epoxy-mimic resins, such as those based on bisphenols and other bisphenol A (BPA) replacements; or combinations thereof. Suitably, the crosslinker material, when present, may be selected from hydroxy (alkyl) amide resins, such as β-hydroxy (alkyl) amide resins and/or hydroxy(alkyl) urea resins and/or carbodiimide resins. Suitably, the crosslinker material, when present, may be selected from hydroxy (alkyl) amide resins, such as β-hydroxy (alkyl) amide resins and/or hydroxy(alkyl) urea resins.

Suitably, the crosslinker material, when present, comprises a hydroxyalkylamide material and/or a hydroxyalkylurea material and/or a carbodiimide resin. Suitably, the crosslinker material, when present, comprises a hydroxyalkylamide material and/or a hydroxyalkylurea material.

Suitably, the crosslinker material, when present, may be operable to crosslink the acid functionality on the acid functional polyester material.

The crosslinker material, when present, may contain nitrogen. The crosslinker material, when present, may be in the form of an amine or amide material. The crosslinker material, when present, may comprise a hydroxyl substituted amine or amide material.

Suitably, the crosslinker material, when present, may comprise a hydroxyalkylamide material, such as a β-hydroxyalkylamide material.

The crosslinker material may contain a terminal chemical group as shown in Formula I.

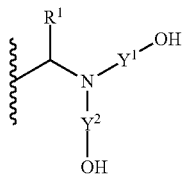

Formula I wherein $R^1$ represents an electron withdrawing group, such as (=O); and $Y^1$ and $Y^2$ each, independently, represents a $C_1$ to $C_3$ alkylene group.

The terminal chemical group of Formula I may be connected to a further chemical structure, not shown. Additionally or alternatively, the chemical group of formula I may be suspended from a carrier substrate, such as a silica carrier substrate, for example.

The hydroxyalkylamide crosslinker may contain a plurality of terminal chemical groups as shown in Formula I. For example, the hydroxyalkylamide crosslinker may contain 2, 3 or 4 terminal chemical groups as shown in Formula I.

The hydroxyalkylamide crosslinker may comprise a moiety according to Formula II:

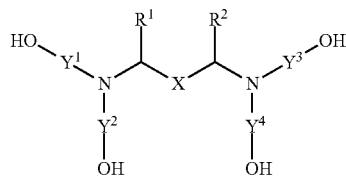

Formula II wherein $R^1$ and $R^2$ with reference to Formula II each, independently, represent an electron withdrawing group, such as (=O); $Y^1$, $Y^2$, $Y^3$ and $Y^4$ with reference to Formula II each, independently, represent a $C_1$ to $C_3$ alkylene group; and X is a $C_2$ to $C_6$ alkylene group.

Suitably, each of $R^1$ and $R^2$ with reference to Formula II represents a (=O) group.

Suitably, each of Y1, Y2, Y3 and Y4 with reference to Formula II represent an ethylene group.

Suitably, X represents a butylene group.

Accordingly, the hydroxyalkylamide crosslinker comprises a material of formula III:

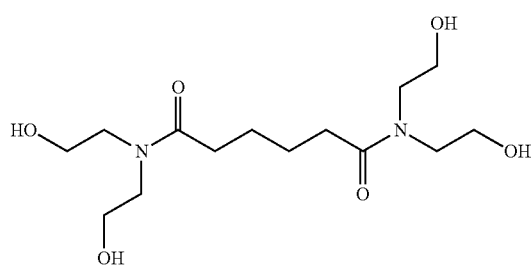

Formula III

The coating composition of the present invention may comprise a commercially available hydroxyalkylamide crosslinker such as, for example, PRIMID XL-552 (available from EMS Chemie); PRIMID QM-1260 (available from EMS Chemie); PRIMID SF-4510 (available from EMS Chemie) and N,N,N',N'-tetrakis(2-hydroxypropyl)adipamide.

The crosslinker may be in the form of a urea material. The crosslinker may comprise a hydroxyl substituted urea material.

Suitably, the crosslinker may comprise a hydroxy functional alkyl polyurea material.

The crosslinker may contain a terminal chemical group as shown in Formula IV.

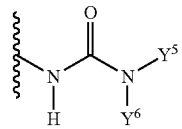

Formula IV wherein $Y^5$ and $Y^6$ each, independently, represent hydrogen, an alkyl or a hydroxy functional alkyl having two or more carbon atoms and at least one of $Y^5$ and $Y^6$ is a hydroxyl functional alkyl having two or more carbon atoms. The $Y^5$ and $Y^6$ groups may exclude ether linkages.

The terminal chemical group of Formula IV may be connected to a further chemical structure, not shown. Additionally or alternatively, the chemical group of Formula IV may be suspended from a carrier substrate, such as a silica carrier substrate, for example.

The crosslinker may contain a plurality of terminal chemical groups as shown in Formula IV. For example, the crosslinker may contain 2 to 6 terminal chemical groups as shown in Formula IV, such as 2, 3 or 4 terminal chemical groups as shown in Formula IV.

The crosslinker material may comprise a moiety according to Formula V:

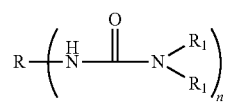

Formula V wherein R with reference to Formula V comprises the residue of an isocyanurate, biuret, allophonate, glycoluril, benzoguanamine, polyetheramine, and/or polymeric moiety having an Mn of 500 or greater; each $R_1$ with reference to Formula V is independently a hydrogen, an alkyl or a hydroxy functional alkyl having 2 or more carbons and at least one $R_1$ with reference to Formula V is a hydroxy functional alkyl having 2 or more carbons; and n is 2-6.

Suitably, the $R_1$ group with reference to Formula V may exclude ether linkages.

The crosslinker may comprise a moiety according to Formula VI:

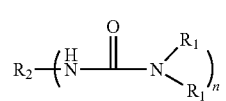

Formula VI wherein $R_2$ with reference to Formula VI comprises a substituted or unsubstituted $C_1$ to $C_{36}$ alkyl group, an aromatic group, or the residue of an isocyanurate, biuret, allophonate, glycoluril, benzoguanamine, polyetheramine, and/or a polymeric moiety having an Mn of 500 or greater; each $R_1$ with reference to Formula VI is independently a hydrogen, an alkyl group having 1 or more carbons, or a hydroxy functional alkyl having 2 or more carbons and at least one $R_1$ with reference to Formula VI is a hydroxy functional alkyl having 2 or more carbons; and n is 2-6.

Suitably, when $R_2$ with reference to Formula VI is a substituted or unsubstituted $C_1$ to $C_{36}$ alkyl group the acid functional polyester material comprises COOH functionality that reacts with the polyurea to form an ester linkage.

Suitably, the $R_1$ group with reference to Formula VI may exclude ether linkages.

It will be understood that when $R_2$ with reference to Formula VI is a substituted or unsubstituted alkyl group, there may be two $R_2$ groups with reference to Formula VI attached to the N, and the two $R_2$ groups with reference to Formula VI may be the same or different. For example, if the hydroxy functional alkyl polyurea is formed from the reaction of dimethyl carbonate with dibutylamine and diisopropanol amine, there will be two $R_2$ groups with reference to Formula VI that will each be C4.

R and $R_2$ with reference to Formula VI may comprise the residue of an isocyanurate, biuret, allophonate, glycoluril, benzoguanamine, polyetheramine and/or polymeric moiety having an Mn of 500 or greater. An isocyanurate will be understood as referring to a compound having three isocyanate groups, typically in ring form, and is sometimes referred to as a trimer. This can include compounds having one or more isocyanurate moieties. Isocyanurates can be purchased from Covestro and Vencore X Chemical. Suitable commercially available isocyanurates include those sold under the trade name DESMODUR such as, for example, DESMODUR N 3300A, DESMODUR N3800, DESMODUR N3790, DESMODUR N3400, DESMODUR N3600, DESMODUR N3900 and DESMODUR RC (commercially available from Covestro), those sold under the trade name VESTANANT such as, for example, VESTANAT T1890/100 (commercially available from Evonik) and those sold under the trade name EASAQUA such as, for example, EASAQUA WT 2102, EASAQUA X D 401, EASAQUA M 501, EASAQUA X D 803, EASAQUA M 502 and EASAQUA X L 600 (commercially available from Vencore X Chemical). Unsaturated isocyanate monomers include but are not limited to 2-acryloyloxyethylisocyanate (AOI), 2-methacryloyloxyethyl isocyanate (MOI), alpha, alpha-dimethyl meta-isopropenyl benzyl isocyanate (TMI), and the adduct of 2-hydroxyethyl acrylate (HEA) and IPDI in 1:1 ratio. A particularly suitable hydroxy functional alkyl polyurea formed from an isocyanurate is shown in Formula VII:

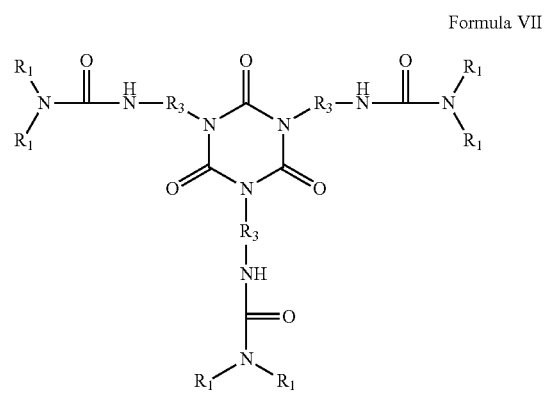

Formula VII wherein $R_1$ with reference to Formula VII is as described above; and each $R_3$ independently comprises an alkyl, aryl, alkylaryl, arylalkyl, alicyclic, and/or polyetheralkyl group.

A particularly suitable hydroxy functional alkyl polyurea formed from a bis-isocyanurate is shown below in Formula VIII:

Formula VIII wherein $R_1$ and $R_3$ with reference to Formula VIII are as described above.

A biuret will be understood as referring to a compound that results upon the condensation of two molecules of urea, and is sometimes referred to as a carbamylurea. Biurets are commercial available from Vencore X Chemical and Covestro as, for example, DESMODUR N-75, DESMODUR N-100, and DESMODUR N-3200, HDB 75B, HDB 75M, HDB 75MX, HDB-LV. A particularly suitable hydroxy functional alkyl polyurea formed from a biuret is shown below in Formula IX:

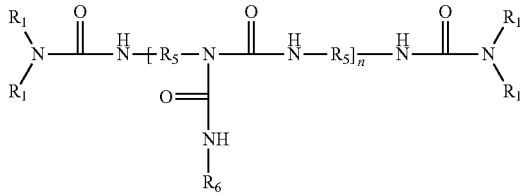

Formula IX wherein $R_1$ with reference to Formula IX is as described above; each $R_5$ independently comprises an alkyl, aryl, alkylaryl, arylalkyl, alicyclic, and/or polyetheralkyl group; and $R_6$ comprises H or an alkyl group.

Uretidione is a dimer of diisocyanate, examples of which include DESMODUR N-3400 polyisocyanate, a blend of the trimer and uretidione of HDI:

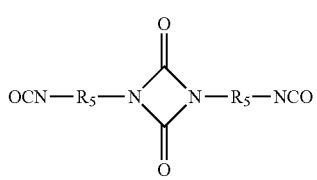

wherein each $R_5$ independently comprises an alkyl, aryl, alkylaryl, arylalkyl, alicyclic, and/or polyetheralkyl group.

An allophonate will be understood as referring to a compound made from urethane and isocyanate. A method for making an allophonate is described at Surface Coating, Vol 1, Raw material and their usage, Landon New York, Chapman and Hall, Page 106. The reaction is generally depicted below in scheme I:

Scheme I

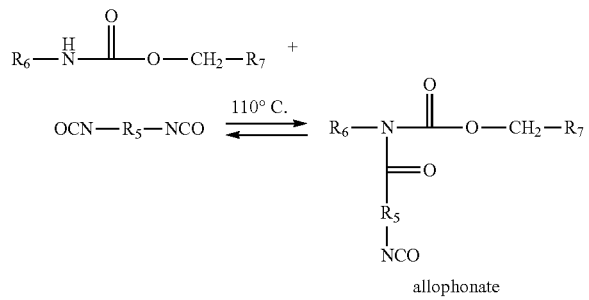

allophonate wherein $R_5$ and $R_6$ with reference to Scheme I are each as described above; and $R_7$ independently comprises the residue of a primary alcohol.

A glycoluril will be understood as referring to a compound composed of two cyclic urea groups joined across the same two-carbon chain, a suitable examples of which includes the below:

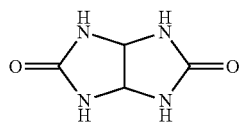

Glycoluril is widely commercially available, such as from Sigma-Aldrich. Benzoguanamine is also known as 6-phenyl-1,3,5-triazine-2,4-diamine and is commercially available from The Chemical Company, Jamestown, R.I.

A polyether amine will be understood as referring to a compound having one or more amine groups attached to a polyether backbone such as one characterized by propylene oxide, ethylene oxide, or mixed propylene oxide and ethylene oxide repeating units in their respective structures, such as, for example, one of the Jeffamine series products. Examples of such polyetheramines include aminated propoxylated pentaerythritols, such as JEFFAMINE XTJ-616, and those represented by Formulas (X) through (VI).

According to Formula (IV) the polyether amine may comprise:

Formula X

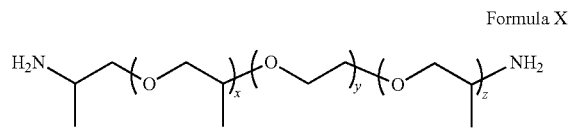

wherein y=0-39, x+z=1-68.

Suitable amine-containing compounds represented by Formula X include, but are not limited to, amine-terminated polyethylene glycol such as those commercially available from Huntsman Corporation in its JEFFAMINE ED series, such as JEFFAMINE HK-511, JEFFAMINE ED-600, JEFFAMINE ED-900 and JEFFAMINE ED-2003, and amine-terminated polypropylene glycol such as in its JEFFAMINE D series, such as JEFFAMINE D-230, JEFFAMINE D-400, JEFFAMINE D-2000 and JEFFAMINE D-4000.

According to Formula XI the polyetheramine may comprise:

Formula XI

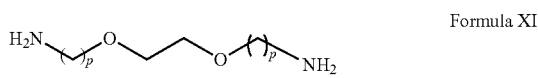

wherein each p independently is 2 or 3.

Suitable amine-containing compounds represented by Formula XI include, but are not limited to, amine-terminated polyethylene glycol based diamines, such as Huntsman Corporation's JEFFAMINE EDR series, such as JEFFAMINE EDR-148 and JEFFAMINE EDR-176.

According to Formula XII the polyetheramine may comprise:

Formula XII

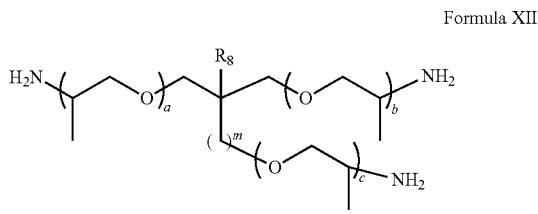

wherein $R_8$ is H or $C_2H_5$, m=0 or 1, a+b+c=5-85.

Suitable amine-containing compounds represented by Formula (VI) include, but are not limited to, amine-terminated propoxylated trimethylolpropane or glycerol, such as Huntsman Corporation's Jeffamine T series, such as JEFFAMINE T-403, JEFFAMINE T-3000 and JEFFAMINE T-5000.

Particularly suitable are di- and tri- amines, such as 4,7,10-trioxa-1,13-tridecanediamine, JEFFAMINE D400, JEFFAMINE D4000, JEFFAMINE D2000, JEFFAMINE T403.

A "polymeric moiety" as used herein in the context of R or $R_2$ with reference to Formulas V to IX refers to any polymer or oligomer to which has been attached two to six hydroxy functional alkyl polyurea groups. The polymer can be, for example, a polyester polyurethane, a polyether polyurethane, or a polyamide polyurethane. The moiety can itself contain functionality, such as acid functionality, hydroxy functionality, and/or amine functionality. The polymeric moiety (which may be oligomeric as noted above) has an Mn of 500 or greater, such as 1000 or greater, 2500 or greater, 4000 or greater, or 5,000 or greater. Mn, as used herein, refers to the number average molecular weight and means the theoretical value as determined by Gel Permeation Chromatography using Waters 2695 separation module with a Waters 410 differential refractometer (RI detector) and polystyrene standards. The Mn values reported according to the invention were determined using this method. Tetrahydrofuran (THF) was used as the eluent at a flow rate of 1 ml min$^{-1}$, and two PL Gel Mixed C columns were used for separation.

In all cases, R and $R_2$ with reference to Formulas V to IX may be substituted or unsubstituted. $R_2$ with reference to Formulas V to IX, as noted above, may also comprise a substituted or unsubstituted $C_1$ to $C_{36}$ alkyl group and/or an aromatic group. For example, the alkyl group may have two to ten carbon atoms, such as six carbon atoms. The alkyl group may derive from an isocyanate, such as a diisocyanate. Suitable examples include isophorone diisocyanate and hexamethylene isocyanate. The aromatic group may derive from an aromatic ring containing isocyanate, suitable examples of which include methylene diphenyl diisocyanate, toluene diisocyanate and tetramethylxylylene diisocyanate.

Certain hydroxy functional alkyl polyureas of, and/or used according to, the invention may be made by reacting an isocyanate-containing compound with amino alcohol. Any isocyanate-containing compound having at least two isocyanate groups can be used, such as any of those described above. It will be appreciated that the "R" or "$R_2$" group with reference to Formulas V to IX will reflect the isocyanate-containing compound selected, if one is used.

Similarly, any amino alcohol having two or more carbon atoms can be used, and the "$R_1$" group with reference to Formulas V to IX will reflect the amino alcohol selected. The amino alcohol can have one, two or more hydroxyl functional groups. One or more amino alcohols can be used, which will result in different $R_1$ groups with reference to Formulas V to IX being present on the polyurea. $R_1$ with reference to Formulas V to IX can also be hydrogen or an alkyl group. Suitable amino alcohols include monoethanol amine, diethanol amine and diisopropanol amine.

The hydroxyl functional alkyl polyureas can be made by reacting amino alcohol with an isocyanate-containing compound in an organic polar solvent, such as alcohol or water. The equivalent ratio of amine to isocyanate may be 2-1:1-2, such as 1:1.

The hydroxy functional alkyl polyureas may be made by alternative methods as well. For example, amino alcohols can react with carbonate to form hydroxylalkyl carbamate, and hydroxylalkyl carbamate can further react with amines to form hydroxy functional alkyl polyureas.

The number-average molecular weight (Mn) of the hydroxy functional alkyl polyurea (even when the polyurea is in the form of a monomer or prepolymer, but not when R or R2 with reference to Formulas V to IX is a polymeric moiety) may be 100 or greater, such as 350 or greater or 1,000 or greater, and/or can be 6,000 or lower, such as 3,000 or lower, or 2,000 or lower. The Mn of the hydroxy functional alkyl polyurea when R or $R_2$ with reference to Formulas V to IX is a polymeric moiety can be 500 or greater, such as 1,000 or greater, 5,000 or greater or 10,000 or greater.

It has surprisingly and advantageously been found by the present inventors that the hydroxyl alkyl urea functional materials typically cure at a lower temperature than, for example, hydroxyalkylamide material, such as a β-hydroxyalkylamide material.

The crosslinker may be in the form of a carbodiimide resin. The crosslinker may comprise a polycarbodiimide. Suitably, the crosslinker may comprise a polycarbodiimide having the following structural units (XIII) or (XIV) including mixtures thereof:

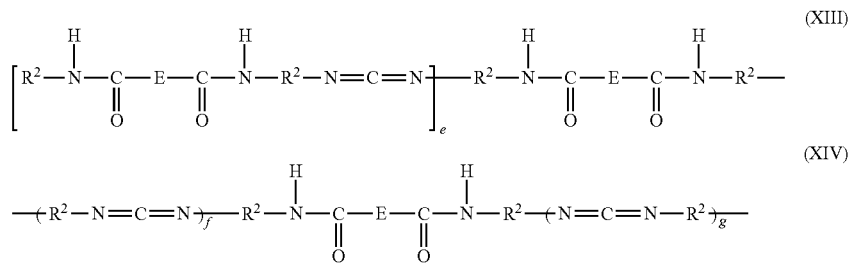

where e is an integer of from 2 to 20; f and g are each at least 1, and f+g is an integer up to 20; E is a radical selected from

where $R^2$ with reference to structural units (XIII) or (XIV) comprises a cyclic radical and $R^3$ with reference to (XV) and (XVI) is a linear hydrocarbon radical containing at least 4 carbon atoms and $R^4$ with reference to (XVI) is hydrogen or an alkyl radical.

The polycarbodiimides may be prepared by reacting an organic group containing a polyisocyanate in the presence of a suitable catalyst to form a polycarbodiimide having terminal NCO-functionality, wherein an active hydrogen-containing compound is added before, during or after polycarbodiimide formation.

The polyisocyanate can be an aliphatic, including cycloaliphatic, or an aromatic polyisocyanate or mixture of the two. Aliphatic including cycloaliphatic polyisocyanates and alkaryl polyisocyanates are particularly suitable. The polyisocyanates can contain from 2 to 4, such as 2 isocyanate groups per molecule. Examples of suitable higher polyisocyanates are 1,2,4-benzene triisocyanate and polymethylene polyphenyl isocyanate. Examples of suitable aromatic diisocyanates are 4,4'-diphenylmethane diisocyanate, 1,3-phenylene diisocyanate, 1,4-phenylene diisocyanate and tolylene diisocyanate. Examples of suitable aliphatic diisocyanates are straight chain aliphatic diisocyanates such as 1,4-tetramethylene diisocyanate and 1,6-hexamethylene diisocyanate and alkaryl polyisocyanates such as m-tetramethylxylene diisocyanate. Also, cycloaliphatic diisocyanates can be employed. Examples include 1,4-cyclohexyl diisocyanate, isophorone diisocyanate, alpha, alpha-xylylene diisocyanate and 4,4-methylene-bis(cyclohexyl isocyanate). Substituted organic group-containing polyisocyanates can also be used in which the substituents are nitro, chloro, alkoxy and other groups that are not reactive with hydroxyl groups or active hydrogens and provided the substituents are not positioned to render the isocyanate group unreactive.

The active hydrogen-containing compound used in the preparation of the polycarbodiimide is suitably a chain extender or spacer linking polyisocyanates together to form NCO-adducts or to link NCO-functional polycarbodiimides together. Any suitable organic compound containing active hydrogens may be used. The term "active hydrogen atoms" refers to hydrogens which, because of their position in the molecule, display activity according to the Zerewitinoff test.

Accordingly, active hydrogens include hydrogen atoms attached to oxygen or nitrogen, and thus useful compounds will include those having at least two of these groups (in any combination):

—OH, and —NH$_2$

The moieties attached to each group can be aliphatic, including cycloaliphatic, aromatic, or of a mixed type with aliphatic being particularly suitable.

The active hydrogen-containing material can contain from 2 to 4, particularly suitable 2 active hydrogens per molecule.

Examples of such compounds include amines, which includes polyamines, aminoalcohols, mercapto-terminated derivatives, and alcohols that includes polyhydroxy materials (polyols) that are particularly suitable because of the ease of reaction with polyisocyanates. Also polyols generally give no side reactions, giving higher yields of urethane product with no by-product and the products are hydrolytically stable. Also, with regard to polyols, there are a wide variety of materials available which can be selected to give a wide spectrum of desired properties. In addition, the polyols have desirable reaction rates with polyisocyanates. Both saturated and unsaturated active hydrogen-containing compounds can be used, but saturated materials are particularly suitable because of superior coating properties.

The polyhydroxyl materials or polyols can be either low or high molecular weight materials and in general will have average hydroxyl values as determined by ASTM designation E-222-67, Method B, of 2000 and below, such as between 2000 and 10. The term "polyol" is meant to include materials having an average of two or more hydroxyl groups per molecule.

The polyols include low molecular weight diols, triols and higher molecular weight polyols, low molecular weight amide-containing polyols and higher polymeric polyols such as polyester polyols, polyether polyols, polycarbonate polyols and hydroxy-containing (meth)acrylic polymers. The polymers typically have hydroxyl values of from 10 to 180. Also, the polymers typically have number average molecular weights of 96 to 10,000 Da.

The low molecular weight diols, triols and higher alcohols useful in the instant invention are known in the art. They have hydroxy values of 200 or above, usually within the range of 200 to 2000. Such materials include aliphatic polyols, particularly alkylene polyols containing from 4 to 18 carbon atoms. Examples include 1,4-butanediol and 1,6-hexanediol. Also useful are polyols containing ether linkages such as diethylene glycol and tetraethylene glycol.

To form the polycarbodiimide, the polyisocyanate with or without the active hydrogen-containing compound may be condensed with the elimination of carbon dioxide to form the polycarbodiimide, that is, a polymer containing $[N=C=N]_n$ units where n with reference to the $[N=C=N]=2$ to 20, such as 2 to 10.

The condensation reaction is typically conducted by taking the solution of the polyisocyanate and heating in the presence of suitable catalyst. Examples of catalyst include 1-ethyl-3-pholine, 1-ethyl-3-methyl-3-pholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the polyisocyanate being used. A concentration range of 0.05-5 parts of catalyst per 100 parts of adduct is generally suitable.

The resulting polycarbodiimide has terminal NCO groups that can then be reacted with an active hydrogen-containing hydrophilic compound.

The hydrophilic compound may be a polyether alcohol or polyether amine or mixtures thereof having a polyether backbone, typically based on ethylene oxide or mixed ethylene oxide and propylene and having a molecular weight greater than 500, such as at least 1000 on a number average basis. Typical alcohols and amines have the following structural formula:

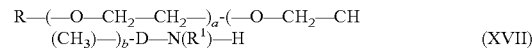

(XVII)

or

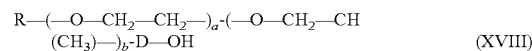

(XVIII)

where R with reference to formulas (XVII) and (XVIII) is $C_1$ to $C_4$ alkyl; a with reference to formulas (XVII) and (XVIII) is 5 to 50 and b with reference to formulas (XVII) and (XVIII) is 0 to 35, and when b with reference to formulas (XVII) and (XVIII) is present the mole ratio of a to b with reference to formulas (XVII) and (XVIII) is at least 1:1; $R^1$ with reference to formula (XVIII) is hydrogen or a hydrocarbon radical and D with reference to formulas (XVII) and (XVIII) is a divalent linking group or a chemical bond.

Reaction of the polyether alcohol or amine with the NCO-containing carbodiimide may be conducted with a stoichiometric equivalent of amine to NCO equivalents or a slight excess of alcohol or amine and at a temperature typically from 80 to 110° C. until an IR spectrum of the reaction mixture indicates substantially no remaining NCO functionality.

Depending on when the active hydrogen chain extender or spacer is used in the reaction, the polycarbodiimide has a structure such that each carbodiimide unit or polycarbodiimide unit is attached to a unit selected from urethane, thiourethane urea, thiourea and a hydrophilic unit occurs at one or terminal positions of the polycarbodiimide via a urethane or urea linkage.

Typically, the polycarbodiimide has a weight average molecular weight of 2600 to 12,000, such as 3000 to 10,000, and a diimide equivalent weight (number average molecular weight/number of carbodiimide groups) of at least 600, such as 600 to 2000.

When the active hydrogen chain extender is added before or during polycarbodiimide formation, that is, is used to chain extend a polyisocyanate to form an NCO-adduct, the polycarbodiimide can be represented from the following structural formula when the polyisocyanate and the active hydrogen-containing compound are difunctional:

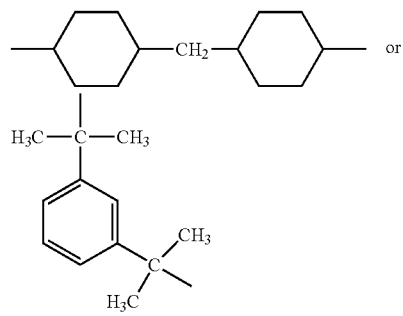

or $R^3$ with reference to formula (XX) and (XXI) is a linear hydrocarbon radical optionally including hetero atoms containing at least 4 carbon atoms such as a polyethylene group having a number average molecular weight of 96 to 10,000. $R^4$ with reference to formula (XXI) is hydrogen or a hydrocarbon radical such as alkyl containing from 1 to 4 carbon atoms. Y with reference to formula (XIX) is a radical of the structure:

$$R\text{—}(\text{—O—CH}_2\text{—CH}_2\text{—})_a\text{-}(\text{—O—CH}_2\text{—CH}(\text{CH}_3)\text{—})_b\text{-D—N}(R^1)\text{—C(O)—NH—} \qquad (XXII)$$

or $$R\text{—}(\text{—O—CH}_2\text{—CH}_2\text{—})_a\text{-}(\text{—O—CH}_2\text{—CH}(\text{CH}_3)\text{—})_b\text{-D—O—C(O)—NH—} \qquad (XXIII)$$

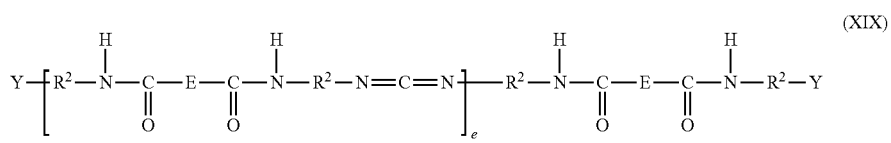

(XIX)

where e with reference to formula (XIX) is an integer of from 2 to 20, such as 2 to 10; E with reference to formula (XIX) is a radical selected from

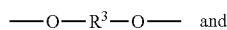 and (XX)

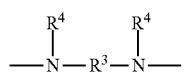

(XXI)

where $R^2$ with reference to formula (XIX) is a cyclic radical such as a cycloaliphatic or an alkaryl radical that may contain 6 to 20 carbon atoms such as those of the structure:

where R with reference to formula (XXII) and (XXIII) is $C_1$ to $C_4$ alkyl; a with reference to formula (XXII) and (XXIII) is 5 to 50 and b with reference to formula (XXII) and (XXIII) is 0 to 35, and when b with reference to formulas (XXII) and (XXIII) is present the mole ratio of a to b with reference to formulas (XXII) and (XXIII) is at least 1:1; $R^1$ with reference to formula (XXII) is hydrogen or a hydrocarbon radical and D with reference to formula (XXII) and (XXIII) is a divalent linking group or a chemical bond.

When the active hydrogen chain extender is added after polycarbodiimide formation, that is, is used to chain extend an NCO-functional polycarbodiimide, the polycarbodiimide can be represented from the following structural formula when the NCO-functional polycarbodiimide and the active hydrogen-containing compound are difunctional.

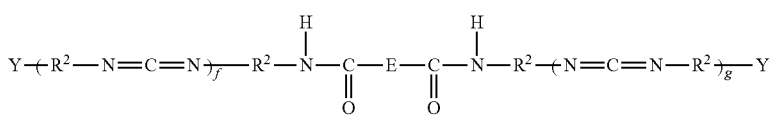

(XXIV)

where f and g with reference to formula (XXIV) are each at least 1, and f+g with reference to formula (XXIV) is an integer up to 20 such as up to 10; E with reference to formula (XXIV) is a radical selected from

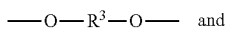 (XXV)

and

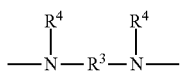 (XXVI)

where $R^2$, $R^3$, $R^4$ and Y with reference to formulas (XXIV), (XXV) and (XXVI) have the meanings mentioned above for (XIX).

Organic solvent can optionally be present in the synthesis of the polycarbodiimide. Polar water miscible solvents such as N-methyl pyrrolidone can be used in amounts of about 5-25 percent by weight based on weight of the reaction mixture.

The powder component of the present invention may comprise any suitable weight ratio of acid functional polyester material to crosslinker, when present. The powder component may have a weight ratio of acid functional polyester material to crosslinker, when present, from to 50:1 to 1:1, suitably from 25:1 to 1:1, such as from 20:1 to 5:1, or even from 15:1 to 5:1. Suitably, the powder may have a weight ratio of acid functional polyester material to crosslinker, when present, of 10:1.

The powder component of the present invention may comprise any suitable amount of crosslinker material, when present. The powder component may comprise from 1 to 20 wt %, suitably from 1.5 to 15 wt %, such as from 2 to 10 wt %, or even from 2.5 to 7.5 wt % of the crosslinker material, when present, based on the total solid weight of the coating composition.

The powder component may comprise at least 1 wt %, suitably at least 1.5 wt %, such as at least 2 wt %, or even at least 2.5 wt % of the crosslinker material, when present, based on the total solid weight of the coating composition. The powder component may comprise up to 20 wt %, suitably up to 15 wt %, such as up to 10 wt %, or even up to 7.5 wt % of the crosslinker material, when present, based on the total solid weight of the coating composition. The powder component may comprise from 1 to 20 wt %, suitably from 1.5 to 20 wt %, such as from 2 to 20 wt %, or even from 2.5 to 20 wt % of the crosslinker material, when present, based on the total solid weight of the coating composition. The powder component may comprise from 1 to 15 wt %, suitably from 1.5 to 15 wt %, such as from 2 to 15 wt %, or even from 2.5 to 15 wt % of the crosslinker material, when present, based on the total solid weight of the coating composition. The powder component may comprise from 1 to 10 wt %, suitably from 1.5 to 10 wt %, such as from 2 to 10 wt %, or even from 2.5 to 10 wt % of the crosslinker material, when present, based on the total solid weight of the coating composition. The powder component may comprise from 1 to 7.5 wt %, suitably from 1.5 to 7.5 wt %, such as from 2 to 7.5 wt %, or even from 2.5 to 7.5 wt % of the crosslinker material, when present, based on the total solid weight of the coating composition.

The powder component of the present invention has an average particle size of less than 15 microns (μm). The powder component may have an average particle size of less than 12 μm, suitably, less than 10 μm, such as less than 7.5 μm, or even less than 5 μm. For the avoidance of doubt the term "less than" includes particles having the stated average particle size. For example, "less than 15 μm" refers to particles having an average particle size of 15 μm as well as those having an average particle size below this value.

The average particle size of the powder component may be measured by any suitable method. Methods to measure the average particle size of the powder component will be well known to a person skilled in the art. Suitably, the average particle size of the powder component is measured by the Hegman scale according to ASTM D1210-05. The Hegman scale runs from 0 (zero), wherein the particle size is >100 microns (μm), to 8 (eight), wherein the particle size is too small to be measured in microns (μm). The measurement is taken by drawing down a sample on a grind block, the face of which is surfaced such that particles of a certain size will visibly protrude on the block at the designated intervals.

It will be appreciated by a person skilled in the art that the Hegman scale may suitably be used to evaluate the degree of dispersion of a powder component in a liquid carrier. For example, the Hegman scale denotes the fineness of the dispersed powder component, i.e. the degree of dispersion and consistency of particle size. For example, a material having a Hegman value of 0 (zero) has typically completely lost its quality of dispersion and the average particle size of the material is generally 100 microns (μm) or greater.

All values for the average particle size of the powder component reported herein were measured this way.

Particles having these sizes may be produced by any suitable method. Suitable methods will be well known to a person skilled in the art. Examples of suitable methods include, but are not limited to, cold grinding, milling and sieving methods.

The powder component may comprise any suitable amount of acid functional polyester material. The powder component may comprise from 10 to 99 wt %, suitably from 25 to 99 wt %, such as from 50 to 99 wt % of even from 60 to 99 wt % of the acid functional polyester material based on the total solid weight of the coating composition.

The coating compositions of the present invention comprise a liquid carrier in which the powder component, such as acid functional polyester materials, are dispersed. For the avoidance of doubt, a dispersion is a powder suspended in a liquid. The coating compositions may comprise any suitable liquid carrier. The liquid carrier may comprise water, an organic solvent, a mixture of water and one or more organic solvent(s) or a mixture of organic solvents. Suitably, the liquid carrier may comprise water.

It has advantageously been found by the present inventors that the acid functional polyester materials of the present invention are surprisingly hydrolytically stable.

Suitably, the liquid carrier may have sufficient volatility to essentially entirely evaporate from the coating composition during the curing process. As a non-limiting example, the curing process may be by heating at 130-230° C. for 1-15 minutes.

Suitable organic solvents include, but are not limited to one or more of the following: aliphatic hydrocarbons such as mineral spirits and high flash point naphtha; aromatic hydrocarbons such as benzene; toluene; xylene; solvent naphtha 100, 150, 200; those available from Exxon-Mobil Chemical Company under the SOLVESSO trade name; alcohols such as ethanol; n-propanol; isopropanol; and n-butanol; ketones such as acetone; cyclohexanone; methylisobutyl ketone; methyl ethyl ketone; esters such as ethyl acetate; butyl acetate; n-hexyl acetate; glycols such as butyl glycol; glycol ethers such as methoxypropanol; ethylene glycol monomethyl ether; ethylene glycol monobutyl ether and combinations thereof.

The liquid coating composition may comprise any suitable amount of liquid carrier. The liquid coating composition may comprise from 10 to 99 wt %, suitably from 20 to 90 wt %, such as from 30 to 80 wt %, or even from 40 to 70 wt % liquid carrier based on the total weight of the coating composition. The liquid coating composition may comprise from 50 to 70 wt % liquid carrier based on the total weight of the coating composition.

The liquid coating compositions of the present invention may comprise any suitable amount of the powder component. The liquid coating compositions may comprise from 1 to 99 wt %, suitably from 10 to 80 wt %, such as from 20 to 70 wt %, or even from 20 to 50 wt % of the powder component based on the total weight of the liquid coating composition. The liquid coating compositions may comprise from 20 to 40 wt % of the powder component based on the total weight of the liquid coating composition.

The liquid coating compositions of the present invention may further comprise one or more pigment and/or filler. The liquid coating compositions may comprise a single pigment or filler or a mixture of pigments and/or fillers. Suitable pigments include, but are not limited to, the following: titanium dioxide; ultramarine blue; phthalocyanines, such as phthalocyanine blue and phthalocyanine green; anthraquinones; quinacridones; thioindigos; carbon black; graphite fibrils; iron oxides, such as black iron oxide; chromium green oxide; ferried yellow; quindo red; or combinations thereof. Suitable fillers include, but are not limited to, the following: barium sulphate; silicas, such as precipitated silicas and clay; or combinations thereof.

Suitably, the liquid coating compositions may comprise titanium dioxide, barium sulphate or a combination thereof. Suitably, the liquid coating compositions may comprise titanium dioxide and barium sulphate.

The pigment and/or filler, when present, may be used in the liquid coating compositions in any suitable amount. The pigment and/or filler, when present, may be used in the liquid coating compositions in amounts from 0 to 50 wt %, suitably from 0 to 40 wt %, such as from 0 to 30 wt %, or even from 0 to 25 wt % based on the total solid weight of the coating composition.

It will be appreciated by a person skilled in the art that the pigment and/or filler, when present, may be present in the powder component, the liquid carrier or the powder component and the liquid carrier.

The coating composition may further comprise one or more catalysts. The coating composition may comprise any catalyst suitable to catalyse the reaction between the acid functional polyester material and the β-hydroxyalkylamide crosslinker. Suitable catalysts will be well known to a person skilled in the art. Examples of suitable catalysts include, but are not limited to, the following: organic tin compounds, such as tin (II) salts of carboxylic acids, for example, tin (II) acetate, tin (II) octonoate, tin (II) ethylhexanoate and tin (II) laurate, tin (IV) compounds, for example, dibutyltin oxide, dibutyltin dichloride, dibutyltin diacetate, dibutyltin dilaurate, dibutyltin maleate and dioctyltin diacetate; tertiary amines, such as diazabicyclo[2.2.2]octane and 1,5-diazabicyclo[4.3.0]non-5-ene; and combinations thereof.

It will be appreciated by a person skilled in the art that the curing catalyst, when present, may be present in the powder component, the liquid carrier or the powder component and the liquid carrier.

The liquid coating compositions of the present invention may optionally comprise a further additive or combination of additives. The liquid coating compositions may optionally comprise any suitable additive or combination of additives. Suitable additives will be well known to the person skilled in the art. Examples of suitable additives include, but are not limited to the following: lubricants; diluents; plasticisers; surfactants; stabilising agents; flow control agents; thixotropic agents; and combinations thereof.

Suitable lubricants will be well known to the person skilled in the art. Suitable examples of lubricants include, but are not limited to one or more of the following: carnauba wax and polyethylene type lubricants. The lubricant, when present, may be used in liquid coating composition in amounts of at least 0.01 wt % based on the total solid weight of the coating composition.

Surfactants may optionally be added to the liquid coating composition in order to aid in flow and wetting of the substrate. Suitable surfactants will be well known to the person skilled in the art. It will be appreciated by a person skilled in the art that the liquid coating composition is chosen to be compatible with food and/or beverage container applications. Suitable surfactants include, but are not limited to one or more of the following: alkyl sulphates (e.g., sodium lauryl sulphate); ether sulphates; phosphate esters; sulphonates; and their various alkali, ammonium, amine salts; aliphatic alcohol ethoxylates; alkyl phenol ethoxylates (e.g. nonyl phenol polyether); salts and/or combinations thereof. The surfactants, when present, may be used in the liquid coating composition in amounts from 0.01 to 10 wt % based on the total solid weight of the coating composition.

Suitable flow control agents will be well known to a person skilled in the art. Suitable flow control agents include, but are not limited to, the following: acrylate polymers, such as polylauryl acrylate, polybutyl acrylate, poly(2-ethylhexyl) acrylate, poly(ethyl-2-ethylhexyl) acrylate, polylauryl methacrylate and polyisodecenyl methacrylate; fluorinated polymers, such as an ester of polyethylene glycol or polypropylene glycol and fluorinated fatty acids, for example, an ester of polyethylene glycol of a molecular weight of over 2,500 Da and perfluorooctanoic acid; polymeric siloxanes, such as polymeric siloxanes of a molecular weight of over 1,000 Da, for example, poly(dimethylsiloxane) and poly(methylphenylsiloxane); and combinations thereof. The flow control agents, when present, may be used in the liquid coating composition in amounts from 0.01 to 10 wt %, suitably from 0.1 to 5 wt %, such as from 0.5 to 4 wt %, or even from 1 to 3 wt % based on the total solid weight of the coating composition.

It will be appreciated by a person skilled in the art that further additives or combination of additives, when present, may be present in the powder component, the liquid carrier or the powder component and the liquid carrier.

The liquid coating compositions according to the present invention are substantially free of bisphenol A (BPA) and derivatives thereof. The liquid coating compositions may be essentially free or may be completely free of bisphenol A (BPA) and derivatives thereof. Derivatives of bisphenol A include, for example, bisphenol A diglycidyl ether (BADGE). The liquid coating compositions according to the present invention are also substantially free of bisphenol F (BBF) and derivatives thereof. The liquid coating compositions may be essentially free or may be completely free of bisphenol F (BPF) and derivatives thereof. Derivatives of bisphenol F include, for example, bisphenol F diglycidyl ether (BPFG). The compounds or derivatives thereof mentioned above may not be added to the composition intentionally but may be present in trace amounts because of unavoidable contamination from the environment. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. By "Completely free" refers to coating compositions, or components thereof, containing less than 20 parts per billion (ppb) of any of the compounds or derivatives thereof mentioned above.

The liquid coating compositions of the present invention may be substantially free, may be essentially fee or may be completely free of dialkyltin compounds, including oxides or other derivatives thereof. Examples of dialkyltin compounds include, but are not limited to one or more of the following: dibutyltindilaurate (DBTDL); dioctyltindilaurate; dimethyltin oxide; diethyltin oxide; dipropyltin oxide; dibutyltin oxide (DBTO); dioctyltinoxide (DOTO) or combinations thereof. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. By "Completely free" refers to coating compositions, or components thereof, containing less than 20 parts per billion (ppb) of any of the compounds or derivatives thereof mentioned above.

The liquid coating compositions of the present invention may be substantially free, may be essentially fee or may be completely free of formaldehyde or sources thereof. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. By "Completely free" refers to coating compositions, or components thereof, containing less than 20 parts per billion (ppb) of any of the compounds or derivatives thereof mentioned above.

It will be appreciated by a person skilled in the art that the crosslinking material, when present, may be selected so as to be substantially free, essentially fee or completely free of formaldehyde or sources thereof.

The liquid compositions of the present invention may be substantially free, may be essentially free or may be completely free of bromine. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. By "Completely free" refers to coating compositions, or components thereof, containing less than 20 parts per billion (ppb) of any of the compounds or derivatives thereof mentioned above.

The liquid coating composition of the present invention is a curable coating composition. "Curable coating compositions" and like terms as used herein, refers to coating compositions that include an initial powder state, i.e. the powder component, and a final state in which the coating composition has been transformed into a substantially continuous, coalesced state.

The liquid coating composition of the present invention may be cured by any suitable method. The liquid coating composition may be cured by heat curing or by chemical curing, suitably by heat curing. The liquid coating composition, when heat cured, may be cured at any suitable temperature. The liquid coating composition, when heat cured, may be cured at temperatures from 50 to 350° C., suitably from 100 to 320° C., such as from 150 to 300° C., or even from 200 to 300° C.

The liquid coating compositions according to the present invention are applied to metal substrates. Examples of suitable metal substrates include, but are not limited to, food and/or beverage containers, components used to fabricate such containers or monobloc aerosol cans and/or tubes. Suitably, the food and/or beverage container may be a can. Examples of cans include, but are not limited to one or more of the following, two-piece cans, three-piece cans and the like. Suitable examples of monobloc aerosol cans and/or tubes include, but are not limited to, deodorant and hair spray containers. Monobloc aerosol cans and/or tubes may be aluminium monobloc aerosol cans and/or tubes.

The metal substrate may be formed from any suitable material. Suitable materials will be well known to a person skilled in the art. Suitable examples include, but are not limited to one or more of the following: steel; tinplate; tinplate pre-treated with a protective material such as chromium, titanium, titanate or aluminium; tin-free steel (TFS); galvanised steel, such as for example electro-galvanised steel; aluminium; aluminium alloy; and combinations thereof.

The liquid coating compositions of the present invention may be applied to the metal substrate by any suitable method. Methods of applying said liquid coating compositions to the substrate will be well known to a person skilled in the art. Suitable application methods include, but are not limited to one or more of the following: spray coating; roll coating; dipping; brushing.

Suitably, the liquid coating compositions according to the present invention may be applied to the metal substrate by roll or spray for example.

The application of various pre-treatments and coatings to packaging is well established. Such treatments and/or coatings, for example, can be used in the case of metal cans, wherein the treatment and/or coating is used to retard or inhibit corrosion, provide a decorative coating, provide ease of handling during the manufacturing process, and the like. Coatings can be applied to the interior of such cans to prevent the contents from contacting the metal of the container. Contact between the metal and a food or beverage, for example, can lead to corrosion of a metal container, which can then contaminate the food or beverage. This is particularly true when the contents of the can are acidic in nature. The coatings applied to the interior of metal cans also help prevent corrosion in the headspace of the cans, which is the area between the fill line of the product and the can lid; corrosion in the headspace is particularly problematic with food products having a high salt content. Coatings can also be applied to the exterior of metal cans. Certain coatings of the present invention are particularly applicable for use with coiled metal stock, such as the coiled metal stock from which the ends of cans are made ("can end stock"), and end caps and closures are made ("cap/closure stock"). Since coatings designed for use on can end stock and cap/closure stock are typically applied prior to the piece being cut and stamped out of the coiled metal stock, they are typically flexible and extensible. For example, such stock is typically coated on both sides. Thereafter, the coated metal stock is punched. For can ends, the metal is then scored for the "pop-top" opening and the pop-top ring is then attached with a pin that is separately fabricated. The end is then attached to the can body by an edge rolling process. A similar procedure is done for "easy open" can ends. For easy open can ends, a score substantially around the perimeter of the lid allows for easy opening or removing of the lid from the can, typically by means of a pull tab. For caps and closures, the cap/closure stock is typically coated, such as by roll coating, and the cap or closure stamped out of the stock; it is possible, however, to coat the cap/closure after formation. Coatings for cans subjected to relatively stringent temperature and/or pressure requirements should also be resistant to popping, corrosion, blushing and/or blistering.

Accordingly, the present invention is further directed to a package coated at least in part with any of the coating compositions described above. A "package" is anything used to contain another item, particularly for shipping from a point of manufacture to a consumer, and for subsequent storage by a consumer. A package will be therefore understood as something that is sealed so as to keep its contents free from deterioration until opened by a consumer.

The manufacturer will often identify the length of time during which the food or beverage will be free from spoilage, which typically ranges from several months to years. Thus, the present "package" is distinguished from a storage container or bakeware in which a consumer might make and/or store food; such a container would only maintain the freshness or integrity of the food item for a relatively short period. A package according to the present invention can be made of metal or non-metal, for example, plastic or laminate, and be in any form. An example of a suitable package is a laminate tube. Another example of a suitable package is metal can. The term "metal can" includes any type of metal can, container or any type of receptacle or portion thereof that is sealed by the food/beverage manufacturer to minimize or eliminate spoilage of the contents until such package is opened by the consumer. One example of a metal can is a food can; the term "food can(s)" is used herein to refer to cans, containers or any type of receptacle or portion thereof used to hold any type of food and/or beverage. The term "metal can(s)" specifically includes food cans and also specifically includes "can ends" including "E-Z open ends", which are typically stamped from can end stock and used in conjunction with the packaging of food and beverages. The term "metal cans" also specifically includes metal caps and/or closures such as bottle caps, screw top caps and lids of any size, lug caps, and the like. The metal cans can be used to hold other items as well, including, but not limited to, personal care products, bug spray, spray paint, and any other compound suitable for packaging in an aerosol can. The cans can include "two piece cans" and "three-piece cans" as well as drawn and ironed one-piece cans; such one piece cans often find application with aerosol products.

Packages coated according to the present invention can also include plastic bottles, plastic tubes, laminates and flexible packaging, such as those made from PE, PP, PET and the like. Such packaging could hold, for example, food, toothpaste, personal care products and the like.

The coating can be applied to the interior and/or the exterior of the package. The coating could also be applied as a rim coat to the bottom of the can. The rim coat functions to reduce friction for improved handling during the continued fabrication and/or processing of the can. The coating can also be applied to caps and/or closures; such application can include, for example, a protective varnish that is applied before and/or after formation of the cap/closure and/or a pigmented enamel post applied to the cap, particularly those having a scored seam at the bottom of the cap. Decorated can stock can also be partially coated externally with the coating described herein, and the decorated, coated can stock used to form various metal cans.

Metal coils, having wide application in many industries, are also substrates that can be coated according to the present invention. Coil coatings also typically comprise a colorant.

The liquid coating compositions according to the present invention may be applied to the metal substrate to any suitable dry film thickness. The liquid coating compositions may be applied to the metal substrate to a dry film thickness from 0.1 µm (microns) to 300 µm, suitably from 3 µm to 250 µm, such as from 5 µm to 150 µm, or even from 5 µm to 75 µm.

The liquid coating compositions of the present invention may be applied to the metal substrate as a single layer or as part of a multi layer system. The liquid coating compositions of the present invention may be applied to the metal substrate as a single layer. The liquid coating compositions of the present invention may be applied to the metal substrate as the first coat of a multi coat system. Suitably, the liquid coating compositions of the present invention may be applied to the metal substrate as an undercoat or a primer. The second, third, fourth etc. coats may comprise any suitable paint such as those containing, for example, epoxy resins; polyester resins; polyurethane resins; polysiloxane resins; hydrocarbon resins or combinations thereof. The liquid coating compositions of the present invention may be applied on top of another paint layer as part of a multi layer system. For example, the liquid coating compositions of the present invention may be applied on top of a primer. The liquid coating compositions of the present invention may form an intermediate layer or a top coat layer. The liquid coating compositions of the present invention may be applied to the metal substrate once or multiple times. Any or all of the layers may be substantially free, essentially free or completely free of BPA, BPF and derivatives thereof.

The powder component of the present invention may be prepared by any suitable method. For example, the powder component may be prepared by first dry blending the material, such as acid functional polyester material and, if present, the crosslinker, pigment and/or filler, curing agent and additives in a blender. The blender may be operated for any suitable period of time.

Suitably, the blender may be operated for a period of time sufficient to result in a homogeneous dry blend of the materials charged thereto. The homogenous dry blend may then be melt blended in an extruder, such as a twin-screw co-rotating extruder, operated within a temperature range from 80 to 140° C., suitably from 100 to 125° C. The extrudate of the powder component may be cooled and is typically milled to an average particle size as described above.

The liquid coating composition of the present invention may be prepared by any suitable method. The liquid coating composition may be prepared by mixing the powder component in the liquid carrier. The liquid coating composition may be prepared by a method comprising the steps of (i) providing a powder having an average particle size of at least 20 microns (μm) and grinding the powder of step (a) in a liquid carrier.

Thus, according to a second aspect of the present invention there is provided a method for producing a liquid coating composition comprising a powder component dispersed in a liquid component, comprising the steps of:
a) providing a powder having an average particle size of at least 20 microns (μm), and
b) dispersing the powder of step a) in a liquid carrier,
wherein the average particle size of the powder dispersed in the liquid carrier of step (b) is less than 15 microns (μm) and wherein the coating composition is substantially free of bisphenol A (BPA), bisphenol F (BPF), bisphenol A diglycidyl ether (BADGE) and bisphenol F diglycidyl ether (BFDGE).

The powder of step (a) of the second aspect of the present invention may be provided by any suitable method. Examples of suitable methods include, but are not limited to, the following: extrusion followed by grinding, such as cold grinding, milling or sieving methods; or obtaining the powder from a commercial source. Suitably, the powder of step (a) is provided by extrusion followed by grinding, such as cold grinding, milling or sieving methods.

The powder of step (a) of the second aspect of the present invention has an average particle size of at least 20 microns (μm). The powder of step (a) may have an average particle size of at least 25 microns (μm), suitably at least 30 microns (μm), such as at least 40 microns (μm), or even at least 50 microns (μm). The powder of step (a) may have an average particle size of up to 1,000 microns (μm), suitably up to 750 microns (μm), such as up to 500 microns (μm) or even up to 250 microns (μm).

The average particle size of the powder of step (a) of the second aspect of the present invention may be measured by any suitable method. Suitable methods will be well known to a person skilled in the art. The average particle size of the powder of step (a) may be measured by laser diffraction analysis. Suitably, laser diffraction analysis may be performed using a Microtrac S3000 laser diffraction analyser (commercially available from Micrtorac), suitably according to the manufacturer's protocol. All values for the average particle size of the powder of step (a) of the second aspect of the present invention reported herein were measured this way.

A person skilled in the art will appreciate that techniques to measure the average particle size of the powder component of the first aspect of the present invention may also be applied to measure the average particle size of the powder obtained following step (b) of the second aspect of the present invention. Suitably, the average particle size of the powder dispersed in the liquid carrier of step (b) may be measured by the Hegman scale according to ASTM D1210-05. All values for the average particle size of the powder obtained following step (b) of the second aspect of the present invention reported herein were measured this way.

Step (b) may be carried out using any suitable method. Suitable methods will be well known to a person skilled in the art. Step (b) may be carried out using cold-grinding, cryo-grinding, ball milling, kinetic dispersion, stone milling, sand milling or bead milling.

Step (b) may be carried out using a LAU 200 disperser (commercially available from LAU GmbH).

It has surprisingly and advantageously been found by the present inventors that the use of the powders of the present inventions allows, for example, grinding with a liquid carrier in step (b). It will be appreciated by a person skilled in the art that it is not typically possible to, for example, grind a powder into a liquid carrier. Without being bound by theory, this may be as a result of the glass transition temperature (Tg) of the powder component.

It is an advantage of the present invention that the average particle size of the powder dispersed in the liquid carrier of step (b) is smaller than would typically be expected.

According to a further aspect of the present invention there is provided a metal substrate coated on at least a portion thereof with a liquid coating composition comprising a powder component dispersed in a liquid component produced according the method of the second aspect of the present invention.

According to a further aspect of the present invention there is provided food and/or beverage packaging being coated on at least a portion thereof with a liquid coating composition comprising a powder component dispersed in a liquid carrier, wherein the average particle size of the powder dispersed in the liquid carrier is less than 15 microns (μm); wherein the powder component comprises a thermoset resin; wherein the thermoset resin comprises an acid functional polyester material; and wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a monobloc aerosol can and/or tube being coated on at least a portion thereof with a liquid coating composition comprising a powder component dispersed in a liquid carrier, wherein the average particle size of the powder dispersed in the liquid carrier is less than 15 microns (μm); wherein the powder component comprises a thermoset resin; wherein the thermoset resin comprises an acid functional polyester material; and wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided food and/or beverage packaging liquid coating composition, the liquid coating composition comprising a powder component dispersed in a liquid carrier, wherein the average particle size of the powder dispersed in the liquid carrier is less than 15 microns (μm); wherein the powder component comprises a thermoset resin; wherein the thermoset resin comprises an acid functional polyester material; and wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a metal substrate being coated on at least a portion thereof with a liquid coating composition comprising a powder component dispersed in a liquid carrier, wherein the average particle size of the powder dispersed in the liquid carrier is less than 15 microns (μm) and wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided food and/or beverage packaging being coated on at least a portion thereof with a liquid coating composition comprising a powder component dispersed in a liquid carrier, wherein the average particle size of the powder dispersed in the liquid carrier is less than 15 microns (μm), wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a monobloc aerosol can and/or tube being coated on at least a portion thereof with a liquid coating composition comprising a powder component dispersed in a liquid carrier, wherein the average particle size of the powder dispersed in the liquid carrier is less than 15 microns (μm), wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided food and/or beverage packaging liquid coating composition, the liquid coating composition comprising a powder component dispersed in a liquid carrier, wherein the average particle size of the powder dispersed in the liquid carrier is less than 15 microns (μm), wherein the coating composition is substantially free of bisphenol A (BPA), bisphenol F (BPF), bisphenol A diglycidyl ether (BADGE) and bisphenol F diglycidyl ether (BFDGE).

All of the features contained herein may be combined with any of the above aspects and in any combination.

For a better understanding of the invention, and to show how embodiments of the same may be carried into effect, reference will now be made, by way of example, to the following experimental data.

EXAMPLES

Powder Example 1

Powder example 1 was prepared according to the formulation in Table 1 and by the following method. All amounts are given in parts by weight (pbw) unless otherwise specified.

The powder was prepared by pre-mixing the ingredients in a three-blade mixer rotating at 3,500 rpm. The pre-mix was then extruded in a 19 mm dual screw extruder operating at a temperature of 100° C. The extrudate was rapidly cooled and pressed into chip. The chip was micronised to an average particle size of 25 microns (μm) using a Hosokawa Air-Classifying Mill (ACM).

TABLE 1

Formulation of powder example 1

| Component | Amount |
|---|---|
| Polyester Resin [1] (acid value of 35) | 94.2 |
| Primid QM-1260 [2] | 5.8 |
| Total | 100 |

[1] acid functional polyester commercially available from PPG having an acid value of 35 and 100% solid
[2] β-hydroxyalkylamide crosslinker available from EMS

Liquid Coating Example 2

Liquid coating example 2 was prepared according to the formulation in Table 2 and by the following method. All amounts are given in parts by weight (pbw) unless otherwise specified.

The liquid coating was prepared by combining all of the materials. This mixture was then milled with a Lau 200 Disperser for 8 hours and demonstrated a Hegman value of greater than 7.5, as determined by ASTM D1210-05. This corresponds to a particle size of less than 5 microns (μm).

TABLE 2

Formulation of liquid coating example 2

| Component | Amount |
|---|---|
| Deionised water | 85.0 |
| BYK-011 [1] | 0.43 |
| Triton GR-5 [2] | 0.71 |
| Disperbyk 190 [3] | 4.38 |
| Powder example 1 | 47.1 |
| Bentone EW [4] | 0.6 |
| Total | 138.21 |

[1] Defoamer available from BYK
[2] Surfactant available from Dow
[3] Dispersing agent available from BYK
[4] Anti-settle agent available from Elementis The properties of the coatings were tested via the following methods. Results are shown in Table 3.

Test panel preparation: Coated panels were obtained by drawing paints over zirconium treated 5182-H481 aluminum panels using a wire wound rod to obtain dry coating weights of 7.0 mg/square inch (msi). The coated panels were immediately placed into a one-zone, gas-fired, conveyor oven for 10 seconds and baked to a peak metal temperature of 232° C. The baked panels were immediately quenched in water upon exit from the oven. They were then dried and cut into smaller test panels.

Test Methods

MEK Double Rubs: The number of reciprocating rubs required to remove the coating was measured using a rag soaked in methyl ethyl ketone (MEK).

Wedge Bend Test: The flexibility of the coatings was evaluated with a wedge bend test. For this test, coated panels were cut into 2 inch by 4.5 inch pieces, with the substrate grain running perpendicular to the long length of the cut panel. They were then bent over a 0.25 inch metal dowel along the long length of the panel with the coated side facing out. The bent panels were then placed onto a block of metal where a wedge was pre-cut out of it with a taper of 0 to 0.25 inch along a 4.5 inch length. Once placed in the wedge, each bent panel was struck with a block of metal which weighed 2.1 kilograms from a height of 11 inches to form a wedge where one end of the coated metal impinged upon itself and a 0.25 inch space remained on the opposite end. The wedge bent panels were then placed into an aqueous solution of copper sulphate and hydrochloric acid for two minutes to purposely etch the aluminum panel in areas where the coatings failed and cracked. The etched wedge bent panels were then examined through a microscope at 10× power to determine how far the coating had cracked from the impinged end along the bent radii. Results are reported as the percentage of cracked area versus total length of the wedge bent panel.

Boiling Water Tests: The coatings were also evaluated for their ability to adhere to the aluminum panels and to resist blushing in four aqueous solutions as follows:

a) Dowfax Detergent Test: This test is designed to measure the resistance of a coating to a boiling detergent solution. The solution is prepared by mixing 5 grams of DOWFAX 2A1 (available from Dow Chemical) into 3,000 grams of deionized water. Coated strips are immersed into the boiling Dowfax solution for 15 minutes. The strips are then rinsed and cooled in deionized water, dried, and immediately rated for blush as described below.

b) Joy Detergent Test: This test is designed to measure the resistance of a coating to a hot 82° C. Joy detergent solution. The solution is prepared by mixing 30 grams of Ultra Joy Dishwashing Liquid (available from Procter & Gamble) into 3,000 grams of deionized water. Coated strips are immersed into the 82° C. Joy solution for 15 minutes. The strips are then rinsed and cooled in deionized water, dried, and immediately rated for blush as described below.

c) Acetic Acid Test: This test is designed to measure the resistance of a coating to a boiling 3% acetic acid solution. The solution is prepared by mixing 90 grams of glacial acetic acid (available from Fisher Scientific) into 3,000 grams of deionized water. Coated strips are immersed into the boiling acetic acid solution for 30 minutes. The strips are then rinsed and cooled in deionized water, dried, and immediately rated for blush as described below.

d) Deionized Water Retort Test: This test is designed to measure the resistance of a coating to deionized water. Coated strips are immersed into the deionized water and placed in a steam retort for 30 minutes at 121° C. The strips are then cooled in deionized water, dried, and immediately rated for blush as described below.

Blush Resistance: Blush resistance measures the ability of a coating to resist attack by the various testing solutions described above. When the coated film absorbs the test solution, it generally becomes cloudy or looks white. Blush is measured visually using a scale of 1-10 where a rating of "10" indicates no blush and a rating of "0" indicates complete whitening of the film. Blush ratings of at least 6 are typically desired for commercially viable coatings. The coated panel tested was 5×10 cm and the testing solution covered half of the panel being tested such that a comparison between the blush of the exposed portion to the unexposed portion of the panel could be made.

Adhesion: Adhesion testing was performed to assess whether the coating adhered to the substrate. The adhesion test is performed according to ASTM D 3359 Test Method B, using Scotch 610 tape, available from 3M Company of Saint Paul, Minn. Adhesion was assessed visually and was rated on a scale of 1-10 where a rating of "10" indicates no adhesion failure, a rating of "9" indicates 90% of the coating remains adhered, a rating of "8" indicates 80% of the coating remains adhered, and so on.

TABLE 3

| Test Results | | Liquid coating example 2 |
|---|---|---|
| MEK Double Rubs | | 17 |
| Wedge Bend (average % Spotty Failure) | | 12% |
| a) Dowfax | Blush | 6 |
|  | Adhesion | 10 |
| b) Joy | Blush | 6 |
|  | Adhesion | 10 |
| c) Acetic acid | Blush | 4 |
|  | Adhesion | 10 |
| d) Water Retort | Blush | 4 |
|  | Adhesion | 10 |

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A metal substrate coated on at least a portion thereof with a liquid coating composition comprising a powder component dispersed in a liquid carrier,
   wherein the average particle size of the powder dispersed in the liquid carrier is less than 15 microns (μm);
   wherein the powder component comprises a thermoset resin;
   wherein the thermoset resin comprises an acid functional polyester material;
   wherein the coating composition is substantially free of bisphenol A (BPA), bisphenol F (BPF), bisphenol A diglycidyl ether (BADGE) and bisphenol F diglycidyl ether (BFDGE);
   wherein any polyester material in the thermoset resin has an acid number (AN) of at least 25 mg KOH/g; and
   wherein the coating composition is substantially free of formaldehyde.

2. The metal substrate of claim 1, wherein the substrate is a food and/or beverage packaging.

3. The metal substrate of claim 1, wherein the substrate is a monobloc aerosol can and/or tube.

4. The metal substrate of claim 1, wherein the powder component comprises a micronized powder.

5. A metal substrate according to claim 1, wherein the acid functional polyester material comprises the reaction product of a polyacid and a polyol.

6. A metal substrate according to claim 5, wherein the acid functional polyester is formed from a polyacid comprising succinic acid, glutaric acid, adipic acid, heptanoic acid, dodecanedioic acid or combinations thereof.

7. A metal substrate according to claim 5, wherein the acid functional polyester material has an acid number (AN) of at least 25 mg KOH/g.

8. A metal substrate according to claim 5, wherein the acid functional polyester material has a Tg from 20° C. to 150° C.

9. A metal substrate according to claim 1, wherein the powder component further comprises a thermoplastic resin.

10. A metal substrate according to claim 9, wherein the thermoplastic resin comprises a polyolefin resin, an acrylic resins or a combination thereof.

11. A metal substrate according to claim 1, wherein the powder component further comprises a crosslinker material.

12. A metal substrate according to claim 11, wherein the crosslinker comprises a hydroxyalkylamide material and/or a hydroxy functional alkyl polyurea material and/or a carbodiimide resin.

13. A metal substrate according to claim 1, wherein the liquid carrier comprises water, an organic solvent, a mixture of water and one or more organic solvent(s) or a mixture of organic solvents.

14. A metal substrate according to claim 13, wherein the liquid carrier comprises water.

15. A method for producing a liquid coating composition comprising a powder component dispersed in a liquid component, comprising dispersing a powder having an average particle size of at least 20 microns (μm) in a liquid carrier, wherein the average particle size of the powder once dispersed in the liquid carrier is less than 15 microns (μm); wherein the coating composition is substantially free of bisphenol A (BPA), bisphenol F (BPF), bisphenol A diglycidyl ether (BADGE) and bisphenol F diglycidyl ether (BFDGE); wherein the powder comprises a thermoset resin; wherein the thermoset resin comprises an acid functional polyester material; wherein any polyester material in the thermoset resin has an acid number (AN) of at least 25 mg KOH/g;

and wherein the coating composition is substantially free of formaldehyde.

16. The method of claim 15, wherein the powder comprises a micronized powder.

* * * * *